United States Patent
Li et al.

(10) Patent No.: US 7,202,022 B2
(45) Date of Patent: *Apr. 10, 2007

(54) METHOD FOR IDENTIFICATION, SEPARATION AND QUANTITATIVE MEASUREMENT OF NUCLEIC ACID FRAGMENTS

(75) Inventors: Bi-Yu Li, San Diego, CA (US); Xun Wang, San Diego, CA (US); Liang Shi, San Diego, CA (US)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/896,324

(22) Filed: Jun. 29, 2001

(65) Prior Publication Data

US 2003/0148276 A1 Aug. 7, 2003

Related U.S. Application Data

(60) Provisional application No. 60/215,596, filed on Jun. 30, 2000.

(51) Int. Cl.
*C12Q 1/68* (2006.01)
*C12P 19/34* (2006.01)
*C07H 19/00* (2006.01)
*C07H 21/04* (2006.01)

(52) U.S. Cl. .................. 435/6; 435/91.21; 536/22.1; 536/24.33

(58) Field of Classification Search .............. 435/6, 435/69.1, 91.21, 91.2; 536/26.2, 24.2, 23.1, 536/24.33, 22.1
See application file for complete search history.

(56) References Cited

U.S. PATENT DOCUMENTS

| | | | |
|---|---|---|---|
| 5,093,245 A | 3/1992 | Keith et al. | |
| 5,366,877 A | 11/1994 | Keith | |
| 5,459,037 A | 10/1995 | Sutcliffe et al. | |
| 5,695,937 A | 12/1997 | Kinzler et al. | |
| 5,707,807 A * | 1/1998 | Kato ............... | 435/6 |
| 5,712,126 A | 1/1998 | Weissman et al. | |
| 5,866,330 A | 2/1999 | Kinzler et al. | |
| 5,871,697 A | 2/1999 | Rothberg et al. | |
| 5,968,784 A | 10/1999 | Spinella et al. ........ | 435/91.16 |
| 6,100,030 A * | 8/2000 | McCasky Feazel et al. .... | 435/6 |
| 6,184,000 B1 | 2/2001 | Jones et al. ............ | 435/91.41 |
| 6,221,600 B1 * | 4/2001 | MacLeod et al. ........... | 435/6 |
| 6,727,068 B2 * | 4/2004 | Shi et al. ................ | 435/6 |

FOREIGN PATENT DOCUMENTS

| | | | |
|---|---|---|---|
| GB | 2 295 228 | * | 5/1996 |
| GB | 2295011 A | | 5/1996 |
| GB | 2295228 A | | 5/1996 |
| WO | WO 98/51789 | * | 11/1998 |
| WO | WO 98/51789 A2 | | 11/1998 |
| WO | WO 9941415 A1 | * | 8/1999 |
| WO | WO00/40755 | | 7/2000 |
| WO | WO00/53806 | | 9/2000 |

OTHER PUBLICATIONS

Ivanova et al. Identification of differntially expressed genes by restriction endonucleases-based expression fingerprinting. Nucleic Acids Res., vol. 23, No. 15, pp. 2954-2958, 1995.*
Kato k. Description of the entire mRNA population by a 3'end cDNA fragment generated by class IIS restriction enzymes. Nucleic Acids Res., vol. 23, No. 18, pp. 3685-3690, 1995.*
Hedrick et al., Isolation of cDNA clones encoding T cell-specific membrane-associated proteins, *Nature* 308:149-152 (1984).
Koyama et al., Structure of a cytotoxic T-lymphocyte-specific gene shows a strong homology to fibrinogen β and γ chains, *Proc. Natl. Acad. Sci. USA* 84:1609-1613 (1987).
Zipfel et al., Complexity of the Primary Genetic Response to Mitogenic Activation of Human T Cells, *Molecular and Cellular Biology* 9(3):1041-1048 (1989).
Welcher et al., Selective enrichment of specific DNA, cDNA and RNA sequences using biotinylated probes, avidin and copper-chelate agarose, *Nucleic Acids Research* 14(24):1002710044 (1986).
Jeltsch et al, Evidence for an evolutionary relationship among type-II restriction endonucleases Gene, vol. 10, No. 1 (Jul. 4, 1995), pp. 7-16.
Sulston et al, EBI [online] *Homo sapiens BAC clone RP11-479N15 from 2, complete sequence*, Accession No. AC011306, Oct. 6, 1999; http://www.ebi.ac.uk/cgi-bin/emblfetch.
Sulston et al, *Toward a complete human genome sequence Genome Research*, vol. 8, No. 11 (1998), pp. 1097-1108.

* cited by examiner

*Primary Examiner*—Suryaprabha Chunduru
(74) *Attorney, Agent, or Firm*—Jenkins, Wilson, Taylor & Hunt, P.A.

(57) ABSTRACT

The invention relates to a new method for sequence-specific identification, separation and quantitative measurement of nucleic acid fragments. The invention is based on the use of restriction endonucleases that have degenerate bases in their recognition or cleavage sequence. The method has broad applications, including DNA fingerprinting, differential display of mRNA, mutation and polymorphism identification, diagnosis and drug screening.

8 Claims, 4 Drawing Sheets

Fig. 1 Schematic diagram of an example of the invention applying in RNA profiling

METHOD FOR IDENTIFICATION, SEPARATION AND QUANTITATIVE MEASUREMENT OF NUCLEIC ACID FRAGMENTS

CROSS-REFERENCE TO RELATED APPLICATIONS

This application claims priority to U.S. Provisional Patent Application No. 60/215,596, filed Jun. 30, 2000, entitled "Method for Identification, Separation and Quantitative Measurement of Nucleic Acid Fragments" which is incorporated herein by reference in its entirety, including any drawings.

BACKGROUND OF THE INVENTION

1. Field of the Invention

The invention relates to a new method for sequence-specific identification, separation and quantitative measurement of nucleic acid fragments. The invention is based on the use of restriction endonucleases that have degenerate bases in their recognition or cleavage sequence. The method has broad applications, including DNA fingerprinting, differential display of mRNA, mutation and polymorphism identification, diagnosis and drug screening.

2. Description of the Related Art

The field of genomics has taken rapid strides in recent years. It started with efforts to determine the entire nucleotide sequence of simpler organisms such as viruses and bacteria. As a result, genomic sequences of *Hemophilus influenzae* (Fleischman et al., *Science* 269: 496–512 [1995]) and a number of other bacterial strains (*Escherichia coli, Mycobacterium tuberculosis, Helicobacter pylori, Caulobacter jejuni, Mycobacterium leprae*) are now available. This was followed by the determination of complete nucleotide sequence of a number of eukaryotic organisms including budding-yeast (*Saccharomyces cerevisiae*) (Goffeau et al., *Science* 274: 563–567 [1996]), nematode (*Cenorhabditis elegans*) (*C. elegans* sequencing consortium, *Science* 282: 2012–2018 [1998]) and fruit fly (*Drosophila melanogaster*) (Adams et al., *Science* 287: 2185–2195 [2000]). Genome sequencing is rapidly advancing and several genomes are now complete or partially complete, including the human, mouse, and rice genomes.

The availability of complete genomic sequences of various organisms promises to significantly advance our understanding of various fundamental aspects of biology. It also promises to provide unparalleled applied benefits such as understanding genetic basis of certain diseases, providing new targets for therapeutic intervention, developing a new generation of diagnostic tests etc. However, new and improved tools will be needed to harvest and fully realize the potential of genomics research.

The ability to establish differences between DNA samples from two different sources or from the same source but under different developmental or environmental conditions is very important. Subtle differences in the genetic material can often yield valuable information, which can help understand physiological processes as well as can provide powerful techniques with wide applications. The approach has broad applications in areas such as forensic science, determination of predisposition of individuals to certain diseases, tissue typing, molecular taxonomy etc. DNA fingerprinting is already being used for a variety of purposes. Single nucleotide polymorphism (SNP) screening promises to be yet another powerful tool intended for some of these applications.

Just as in the case of DNA profiling, as discussed above, RNA profiling too can yield valuable information with potential use in similar and overlapping applications. Even though the DNA complement or gene complement is identical in various cells in the body of multi-cellular organisms, there are qualitative and quantitative differences in gene expression in various cells. A human genome is estimated to contain roughly about 40,000 genes, however, only about 15,000–20,000 genes are expressed in a given cell (Liang et al., *Science* 257: 967–971 [1992]). Moreover, there are quantitative differences among the expressed genes in various cell types. Although all cells express certain housekeeping genes, each distinct cell type additionally expresses a unique set of genes. Phenotypic differences between cell types are largely determined by the complement of proteins that are uniquely expressed. It is the expression of this unique set of genes and the encoded proteins, which constitutes functional identity of a cell type, and distinguishes it from other cell types. Moreover, the complement of genes that are expressed and their level of expression vary considerably depending on the developmental stage of a given cell type. Certain genes are specifically activated or repressed during differentiation of a cell. The level of expression also changes during development and differentiation. Qualitative and quantitative changes in gene expression also take place during cell division, e.g. in various phases of cell cycle. Signal transduction by biologically active molecules such as hormones, growth factors and cytokines often involves modulation of gene expression. The process of aging is characterized by changes in gene expression.

In addition to the endogenous or internal factors as mentioned above, certain external factors or stimuli, such as environmental factors, also bring about changes in gene expression profile. Infectious organisms such as bacteria, viruses, fungi and parasites interact with the cells and influence the qualitative and quantitative aspects of gene expression. Thus, the precise complement of genes expressed by a given cell type is influenced by a number of endogenous and exogenous factors. The outcome of these changes is critical for normal cell survival, growth, development and response to environment. Therefore, it is very important to identify, characterize and measure changes in gene expression. Not only will the knowledge gained from such analysis further our understanding of basic biology, but it will also allow us to exploit it for various purposes such as diagnosis of infectious and non-infectious diseases and screening to identify and develop new drugs etc.

Besides the conventional, one by one gene expression analysis methods like Northern analysis, RNase protection assays, and RT-PCR, there are several methods currently available to examine gene expression on a genome wide scale. These approaches are variously referred to as RNA profiling, differential display, etc. These methods can be broadly divided into three categories: (1) hybridization-based methods such as subtractive hybridization, microarray etc., (2) cDNA tags: EST, serial analysis of gene expression (SAGE) etc., and (3) fragment size based, often referred to as gel-based methods where differential display is generated upon electrophoretic separation of DNA fragments on a gel such as polyacrylamide.

Although libraries made by subtractive hybridization have been used extensively for the identification and cloning of differentially expressed genes (Wecher et al., *Nucleic*

Acids Res. 14: 10027–10044 [1986]; Hedrick et al., *Nature* 308: 149–153 [1984]; Koyama et al., *Proc. Natl. Acad. Sci. USA* 84: 1609–1613 [1987]; Zipfel et al., *Mol. Cell. Biol.* 9: 1041–1048 [1989]), it is very labor intensive, requires large amount of RNA, and is not amenable to quantitative measurement of gene expression. Moreover, it is not ideally suited for monitoring the expression of a large number of genes in order to generate a genome-wide profile of gene expression. SAGE (see, e.g. U.S. Pat. Nos. 5,695,937 and 5,866,330) provides an alternative method that does not suffer from some of the limitations of subtractive library screening. For example, it allows for quantitative monitoring of global gene expression. However, it too has certain limitations such as higher cost and labor intensiveness, and is not suitable for cloning of identified genes. Moreover, the tag sequences obtained from SAGE library are too short to be used as a gene specific primer or probe.

Gel-based methods (described in U.S. Pat. Nos. 5,871,697, 5,459,037, 5,712,126 and a PCT publication WO 98/51789) address some of the shortcomings of the non-gel-based methods. However, most of them suffer from compromised specificity. Most of the existing gel-based gene expression analysis methods are based on the following principles: cDNAs are first digested by restriction enzyme, ligated with a suitable adapter, then amplified by PCR with selective primers, and fragments resolved on electrophoretic gel. The selection of cDNA population relies upon the annealing of the selective primers to the cDNA fragments and extension by a polymerase during PCR amplification. The method uses sequence variation of neighboring restriction sites in different cDNA fragments. However, PCR is less than ideal in terms of specificity. Depending on the stringency of annealing conditions, one to a few base mismatches are tolerated and primers are extended by the DNA polymerase inspite of less than perfect complementarity between the primer and the template. The variation among the selective primers does not allow stringent conditions for all PCR. The resultant non-specific priming and amplification distorts the profile of amplified fragments, which often does not correlate well with the mRNA profile of the sample.

The individual methods using a gel-based approach suffer from some additional specific disadvantages. For example, a method developed by Curagen (U.S. Pat. No. 5,871,697) requires the use of many different restriction enzymes, the enzyme selection is not flexible, and the reaction set up is rather complicated. Each cDNA sample in this method is separated into 96 pools, and digested by 96 pairs of different 6-base cutter enzymes. It would be difficult to increase the fractionation in this method. A method developed by Digital Gene Technology (U.S. Pat. No. 5,459,037) is based on capturing the 3'-end fragments of cDNAs such that each gene will have only one representative. However, a major disadvantage of this method is its long and complicated procedure, which is not only labor intensive but, more importantly, also decreases the sensitivity and representation of differential display. The technology involves multiple steps such as cDNA synthesis, library construction and cloning, in vitro RNA transcription, a second round cDNA synthesis, and finally PCR. At each step in this convoluted procedure, some bias is introduced that ultimately skews the original representation of transcripts. A PCT publication WO 98/51789 describes a method developed by Display System Technology that utilizes a PCR based profiling approach. The use of only 4 base cutters in this method generates a large number of bands for a specific cDNA species, and introduces redundancy.

Methods for the selection of DNA markers using adaptor molecules and the selective amplification of DNA having a plurality of sites for a specific endonuclease are described in UK Patent Application Nos. GB 2,295,011, published May 15, 1996 and GB 2,295,228, published May 22, 1996. These methods involve the use of starting DNA.

Because of various shortcomings of the currently available technologies there is a need for improved methods of identification, separation and quantitative measurement of nucleic acid fragments. It is the objective of the present invention to provide such a method.

SUMMARY OF THE INVENTION

The present invention provides a method that exploits the advantages provided by restriction enzymes capable of recognizing sequences with variable number of degenerate bases, coupled with selective ligation of the digested DNA with perfectly matching adapter sequences to fractionate DNA fragments into subpools of various size. The methods of the invention preferably start with the conversion of RNA into DNA. The seminal difference between the present invention and methods described in prior art is the use of (1) degeneracy in the overhang region or recognition sequence of certain restriction enzymes, (2) the stringent requirement by DNA ligase of perfect complementarity between the two strands of annealed DNA to covalently close a nick, and (3) the ability to accurately quantitate the amount of polynucleotide present.

The former serves the purpose of effectively fractionating DNA into pools based on the number of degenerate bases (m) and the extent or degree of degeneracy (N) at each degenerate base in the recognition or cleavage sequence of the restriction enzyme used for digestion of DNA. This provides a great degree of flexibility. Depending on the genome complexity of the organism to be used for fingerprinting or profiling, one can choose a restriction enzyme that has a variable number of degenerate bases in the recognition sequence. For example, the use of an enzyme with 1, 2, 3 or 4 fully degenerate bases (m=1–4, N=4 for each degenerate base) in the recognition sequence will allow fractionating the digested DNA into 4, 16, 64 or 256 pools respectively ($N^m$). This can be further fine-tuned by selecting the enzyme with lesser degree of degeneracy (N=2–3) at one or more of the degenerate bases in the recognition sequence. Moreover, choosing a set of other enzymes for double digestion of DNA allows even more fractionation of DNA.

The use of DNA ligase serves the purpose of imparting a high degree of specificity and consistency, and thus maintaining concordance between the actual profile of DNA or cDNA fragments and the ultimate display that is generated by the method. Ligases are highly specific in their hybridization requirement. For example, even one bp mismatch near the ligation site will prevent ligation reaction (see U.S. Pat. Nos. 5,366,877 and 5,093,245). Thus, the use of ligase circumvents the serious drawback of the lack of specificity of other methods that rely on PCR in generating the profile. The ligation of perfectly complementary strands of annealed DNA by DNA ligase distinguishes this method from other methods that rely on the extension of partially matched or mismatched primers and resultant non-specific generation of fragments by DNA polymerase in PCR. The present invention uses PCR only for amplification purpose, and not for the purpose of fractionating DNA into various pools. Moreover, it uses perfectly matched primers for each pool of DNA fragments and thus avoids the problem of non-specific priming and amplification as often observed when degenerate primers are used in PCR. The use of perfectly matched primers permits the use of higher annealing temperature during PCR, which significantly enhances specificity and results in improved concordance between the profile and the actual representation of fragments. Finally, another advantage of the present invention is that it provides an ability to quantitate the results of the methods. Thus, the results can be provided as numerical values and more easily and reliably compared, used and relied upon.

In one aspect, the present invention provides a method for the simultaneous sequence-specific identification and separation of polynucleotide fragments in a polynucleotide population comprising the steps of, preferably converting RNA to DNA and: (a) digesting the polynucleotide population with one or more restriction endonucleases having a degenerate recognition or cleavage sequence comprising a degenerate base, wherein the degenerate base is represented by the formula of $N^m$, where N is the extent of degeneracy, and m is the number of degenerate bases, to produce restriction fragments having $N^m$ different single-stranded overhangs for each restriction endonuclease; (b) ligating the restriction fragments having the same overhangs to a series of adapters whose sequences are complementary to the overhangs; and (c) amplifying the restriction fragments. The polynucleotide may be genomic DNA or cDNA reverse transcribed from an RNA population. In a particular embodiment, at least one of the restriction endonucleases has N value of 2–4; and m value of 1–5, preferably 2–4, and more preferably 2–3. The restriction endonuclease used in the method is a three- to eight-base cutter, preferably four-base cutter. The DNA population may be digested with at least one different restriction endonuclease having a degenerate recognition or cleavage sequence.

In another aspect, the invention provides a method further comprising the step of digesting the restriction fragments obtained in step (a) with one or more further restriction endonucleases producing restriction fragments with single-stranded overhangs different from those produced in step (a). The single-stranded overhangs produced are ligated to adapters whose sequences are complementary to the overhangs.

In yet another aspect, the restriction fragments produced in the method are amplified by polymerase chain reaction (PCR). The PCR primers are designed from the adapters, with at least one of the PCR primers having a detectable label, preferably a fluorescent label. The method provides a further step of detecting the PCR products, preferably by gel electrophoresis, and analyzing for quantitative representation. The PCR products may be isolated, sequenced and cloned into a vector. The vector may be transformed into a host cell in order to express the cDNA and produce a polypeptide. Accordingly, the present invention also provides a host cell transformed with the vector. In a related aspect, the present invention provides a method for screening for interactions between a preselected protein and polypeptide fragments, comprising culturing the host cells transformed with a vector containing PCR amplified insert, under conditions which enable expression of correctly inserted restriction fragments by the host cell, and assaying the interaction of the polypeptide fragments encoded by the restriction fragments with the preselected protein. In a preferred embodiment, the assay is performed by the two-hybrid technique, and the preselected protein is a receptor tyrosine kinase or an enzyme.

The DNA population analyzed by the method of the present invention may be a genomic DNA, derived from a plant, an animal, a bacterium, a yeast or a fungus. Alternatively, the DNA population is cDNA, prepared from RNA derived from a plant, an animal, a bacterium, a yeast or a fungus.

In a different aspect, the present invention provides a method for detecting polymorphism comprising the steps of, preferably converting RNA to DNA and: (a) digesting a polynucleotide population with one or more restriction endonucleases having a degenerate recognition or cleavage sequence comprising a degenerate base, wherein the degenerate base is represented by the formula of $N^m$, where N is the extent of degeneracy, and m is the number of degenerate bases, to produce restriction fragments having $N^m$ different single-stranded overhangs for each restriction endonuclease; (b) ligating the restriction fragments having the same overhangs to a series of adapters whose sequences are complementary to the overhangs; (c) amplifying the restriction fragments; (d) sequencing the amplified restriction fragments; and (e) comparing the sequence of the amplified restriction fragments with the sequence of the same polynucleotide from a different source. The polynucleotide may be genomic DNA or cDNA produced from an RNA population. The RNA used for making cDNA may be mRNA.

In a further aspect, the present invention provides a method for detecting a change in the pattern of RNA expression in a tissue or cell associated with an internal or external factor comprising the steps of: (1) determining the pattern of RNA expression in a first tissue or cell sample not subject to the internal or external change by a method comprising (a) digesting double-stranded cDNA prepared from mRNA isolated from the first sample with one or more restriction endonucleases having a degenerate recognition or cleavage sequence comprising a degenerate base, wherein the degenerate base is represented by the formula of $N^m$, where N is the extent of degeneracy, and m is the number of degenerate bases, to produce restriction fragments having $N^m$ different single-stranded overhangs for each restriction endonuclease; (b) ligating the restriction fragments having the same overhangs to a series of adapters whose sequences are complementary to said overhangs; (c) amplifying the restriction fragments; and (d) displaying the pattern of RNA expression in the first sample; (2) determining the pattern of RNA expression in a second tissue or cell sample subject to the physiological or pathological change by performing the steps (1)(a)–(d) with the second sample; and (3) comparing the first and the second displays to determine the effect of the internal or external factor on the pattern of RNA expression in the tissue. The first sample may be a normal tissue and the second sample may be a disease tissue of the same cell type. Alternatively, the first tissue and the second tissue may represent different stages of development. The tissue is derived from a plant or an animal. The animal tissue may be derived from the cardiovascular system, the pulmonary system, the nervous system, the kidney, the liver, the reproductive system, or the skeletal muscle. The factor is associated with a heart disease, a lung disease, a kidney disease, a neurodegenerative disease, a liver disease, or a disease of the reproductive system. Alternatively, the second tissue is from a tumor representing cancer, derived from breast, ovarian, prostate, stomach, endometrial, salivary gland, lung, kidney, colon, thyroid, pancreatic or bladder. In another alternative, the pattern of RNA expression in the first and second tissues are quantitated prior to comparison.

In a still further aspect, the present invention provides a method for diagnosis of a disease based on detecting a change in the pattern of DNA fragments in a disease tissue or cell sample comprising the steps of: (1) determining the pattern of DNA fragments in the sample by a method comprising, preferably converting RNA to DNA and (a) digesting a DNA isolated from said tissue or cell with one or more restriction endonucleases having a degenerate recognition or cleavage sequence comprising a degenerate base, wherein the degenerate base is represented by the formula of $N^m$, where N is the extent of degeneracy, and m is the number of degenerate bases, to produce restriction fragments having $N^m$ different single-stranded overhangs for each restriction endonuclease; (b) ligating the restriction fragments having the same overhangs to a series of adapters whose sequences are complementary to said overhangs; (c) amplifying the restriction fragments; and (d) displaying the pattern of DNA fragments in the disease tissue or cell sample; (2) determining the pattern of DNA fragments in a normal tissue or cell corresponding to the disease tissue by performing the steps (1)(a)–(d) with the normal tissue; and (3) comparing the profile of DNA fragments in the disease and the normal tissue or cell. The DNA may be genomic DNA or cDNA prepared from RNA. The change in the pattern of DNA fragments is a change in the number and size of DNA fragments corresponding to chromosomal translocation taking place in the disease tissue as compared to the normal tissue. Alternatively, the change in the pattern of DNA fragments is a change in the intensity of DNA fragments corresponding to gene amplification taking place in the disease tissue as compared to the normal tissue. In a further embodiment, the change in the pattern of DNA fragments is quantitated. In another embodiment, the disease is a cancer and the disease tissue is a cancer tissue derived from breast, ovarian, prostate, stomach, endometrial, salivary gland, lung, kidney, colon, thyroid, pancreatic or bladder cancer tissue. In yet another embodiment, the disease is a disease of heart, lung, kidney, liver, nervous system, or reproductive system.

In a related aspect, the present invention provides a method for detecting a change in the pattern of RNA expression in a cell sample in response to an external factor comprising the steps of: (1) determining the pattern of RNA expression in a first tissue or cell sample not subject to said external factor by a method comprising, (a) digesting double-stranded cDNA prepared from RNA isolated from the first sample with one or more restriction endonucleases having a degenerate recognition or cleavage sequence comprising a degenerate base, wherein the degenerate base is represented by the formula of $N^m$, where N is the extent of degeneracy, and m is the number of degenerate bases, to produce restriction fragments having $N^m$ different single-stranded overhangs for each restriction endonuclease; (b) ligating the restriction fragments having the same overhangs to a series of adapters whose sequences are complementary to the overhangs; (c) amplifying the restriction fragments; (d) displaying the pattern of RNA expression in the first sample; and (2) determining the pattern of RNA expression in a second cell sample subjected to the external factor by performing the steps (1)(a)–(d) with the second sample; and (3) comparing the first and the second displays to determine the effect of the external factor on the pattern of RNA expression in the cells. The cell sample is an in vitro grown cell line or a tissue sample derived from an experimental animal. In a particular embodiment, the cell sample is a tissue sample derived from a plant, and the external factor is selected from the group consisting of chemical treatment, drug treatment, irradiation, exposure to light, ozone, and nutrient depletion. In a preferred embodiment, the chemical treatment is with a chemical selected from the group consisting of hormones, herbicides, pesticides and insecticides.

In a different aspect, the present invention provides a method for constructing an expressed sequence tag (EST) library comprising the steps of: (a) digesting double-stranded cDNA prepared from an mRNA population isolated from an eukaryotic source one or more restriction endonucleases having a degenerate recognition or cleavage sequence comprising a degenerate base, wherein the degenerate base is represented by the formula of $N^m$, where N is the extent of degeneracy, and m is the number of degenerate bases, to produce restriction fragments having $N^m$ different single-stranded overhangs for each restriction endonuclease; (b) ligating the restriction fragments having the same overhangs to a series of adapters whose sequences are complementary to the overhangs; (c) amplifying the restriction fragments; and (d) ligating the amplified restriction fragments into a suitable cloning vector. The eukaryotic source is an animal, a plant, a yeast or a fungus.

In yet another aspect, the present invention also provides an isolated nucleic acid molecule comprising an oligonucleotide selected from the group consisting of: SEQ ID NOs: 2–65. The isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity, yet more preferably at least about 99% sequence identity to (a) a DNA molecule of SEQ ID NOs: 2–65, or (b) the complement of the DNA molecule of (a). Also provided is the use of such oligonucleotides in various embodiments of the present invention.

These and other features and advantages of the present invention will be appreciated from the review of the following detailed description of the invention, along with the accompanying figures.

DETAILED DESCRIPTION OF THE PREFERRED EMBODIMENT

Figure 1:
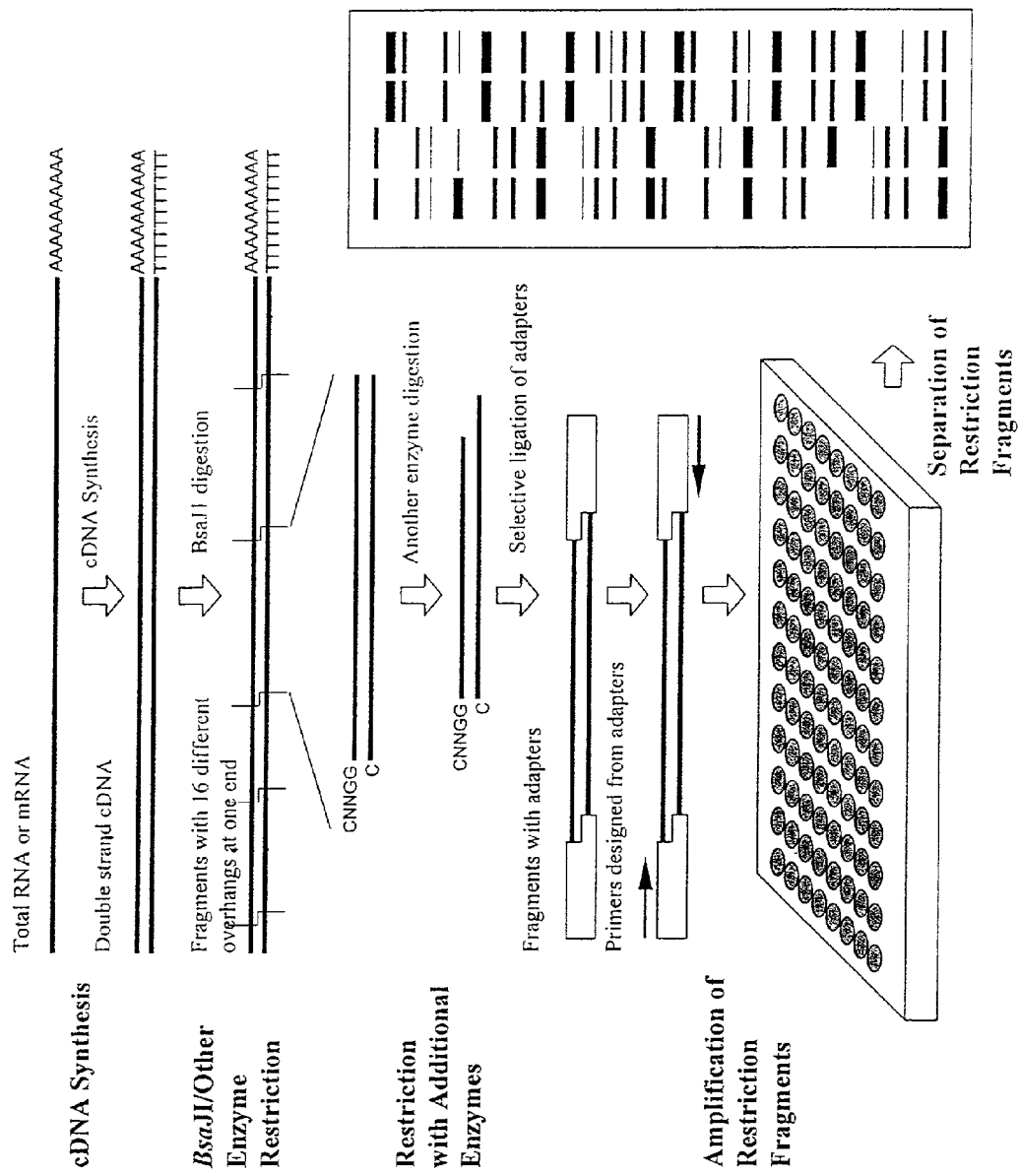
FIG. 1 is a schematic diagram of an example of the invention as applied to mRNA profiling. BsaJI is used as an example of the degenerate RE, which recognizes C/CNNGG and produce 16 different overhangs to fractionate the cDNA population.

Various terms used throughout the application have the same meaning as routinely applied in the relevant art, unless otherwise specified. Most of the general terms in the field of Molecular Biology or Biochemistry are defined in standard texts such as Ausubel et al., Current Protocols in Molecular Biology, Volume 1 and 2, Greene Publishing Ass., and Wiley-Interscience, New York, 1991; Sambrook et al., Molecular Cloning: A Laboratory Manual, $2^{nd}$ edition, Cold Spring Harbor Laboratory Press, Cold Spring Harbor, 1989. The following definitions are offered as a way of general meaning, and are not meant to read as limiting the scope of the invention.

The objective of the invention is to provide a new and versatile method for identification, separation and quantitative measurement of nucleic acid fragments. The application of the method includes, without limitations, differential display of mRNA, DNA fingerprinting, mutation and polymorphism identification, diagnosis, drug screening, molecular taxonomy, gene isolation etc. The disclosed invention will enable the rapid, quantitative and precise determination of gene expression level without the requirement of upfront sequence information. It also provides a tool to identify and clone novel genes.

Definitions

The term "polynucleotide", when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "polypeptide", in singular or plural, is used herein to refer to any peptide or protein comprising two or more amino acids joined to each other in a linear chain by peptide bonds. As used herein, the term refers to both short chains, which also commonly are referred to in the art as peptides, oligopeptides and oligomers, and to longer chains, commonly referred to in the art as proteins. Polypeptides, as defined herein, may contain amino acids other than the 20 naturally occurring amino acids, and may include modified amino acids. The modification can be anywhere within the polypeptide molecule, such as, for example, at the terminal amino acids, and may be due to natural processes, such as processing and other post-translational modifications, or may result from chemical and/or enzymatic modification techniques which are well known to the art. The known modifications include, without limitation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature, such as, for instance, Creighton, T. E., Proteins--Structure And Molecular Properties, 2nd Ed., W. H. Freeman and Company, New York (1993); Wold, F., "Posttranslational Protein Modifications: Perspectives and Prospects," in Posttranslational Covalent Modification of Proteins, Johnson, B. C., ed., Academic Press, New York (1983), pp. 1–12; Seifter et al., "Analysis for protein modifications and nonprotein cofactors," Meth. Enzymol., 182:626–646 (1990), and Rattan et al., Ann. N.Y Acad. Sci., 663:48–62 (1992).

The terms "endonuclease", "restriction endonuclease" and "restriction enzyme" are used interchangeably and in the broadest sense, refer to an enzyme that recognizes double-stranded DNA sequence-specifically and cuts it endonucleotically. It is noted that when a restriction endonuclease is referred to as a "four-base cutter", "six-base cutter", etc. reference is made to the number of nucleotide bases within the recognition sequence of such restriction endonuclease, not including degeneracy. For example, a restriction endonuclease that has the recognition sequence CCNNGG would be referred to as a "four-base cutter". Digestion with a "four-base cutter" restriction endonuclease will result in one cut in every 256 bp fragment of the polynucleotide digested, digestion with as "five-base cutter" restriction endonuclease will result in one cut in every 1024 bases, etc. Accordingly, one factor in choosing a restriction endonuclease will be the desired size and the number of the restriction endonuclease fragments for any particular application.

A restriction endonuclease which has a "degenerate recognition sequence" is one that has one or more degenerate bases in the sequence recognized by such restriction endonuclease, or in the overhang produced by such restriction endonuclease. In this context, the term "degenerate base" means that any of the four bases (A, C, G or T) or a specific subset of four bases (2–3) may be present at the indicated position. The term "number of degenerate bases" refers to the number of nucleotide positions within the recognition or cleavage sequence that may be occupied by degenerate bases. The term "extent of degeneracy" refers to the number of bases that can occupy a given nucleotide position in the recognition or cleavage sequence of a restriction enzyme without significantly affecting the enzymatic activity of such endonuclease. "Full degeneracy" results when any of the four bases (A, C, G or T) can occupy a given degenerate position in the recognition or cleavage sequence. Accordingly, "partial degeneracy" results when a given degenerate position can be occupied by a specific subset of four bases (2–3) such as A/G, C/T, A/C/G or A/T/G etc.

The terms "internal factors" and "endogenous factors" are used interchangeably, and refer to factors or changes brought about internally, i.e. from within the organism, and include, for example, differences in genetic background and various physiological or pathological changes such as those accompanying growth, development, differentiation, cell cycle, signal transduction, and action of biologically active molecules, for instance hormones, growth factors and cytokines. The terms "external factors" and "exogenous factors" are used interchangeably and refer to factors or changes brought about externally, i.e. from outside the organism, and includes, for example, infection by pathogens such as bacteria, viruses, fungi, or insects, and environmental changes such as toxins, heat, radiation, drought, salinity etc.

The term "detectable label" refers to a label which when attached, preferably covalently, provides a means of detection. There are a wide variety of labels available for this purpose. For example, radioactive nuclides such as $^{32}$P or $^{35}$S, or fluorescent dyes are conventionally used to label PCR primers. Chemiluminescent dyes can also be used for the purpose. Some of the commonly used fluorescent dyes are listed in Table 3.

Description of Preferred Embodiments

There are three broad steps in the method disclosed herein:

(1) Generation of DNA fingerprints. Total RNA or enriched population such as poly (A)$^+$ RNA is reverse transcribed to generate double stranded cDNA. This step is bypassed in the case of DNA analysis wherein the starting material is genomic DNA. All the subsequent steps remain the same. The double-stranded DNA is fragmented using a special group of restriction endonucleases which generate overhang or protruding single stranded region at the site of cleavage, and which contains degenerate bases in the recognition sequence or the overhang produced. The fragments so generated will contain differences in the nucleotide sequences of the overhangs, which forms the basis of fractionation of these DNA fragments. For example, if the recognition sequence of a restriction enzyme used contains two degenerate bases, described as N$^m$ wherein N is the extent of degeneracy at a given nucleotide position (e.g. any nucleotide A, G, C or T in this case) and m is the number of degenerate bases (2 in this case), the number of DNA fragments differing in their ends is $4^2$, i.e. 16. Similarly, the use of a restriction enzyme, which has 3 or 4 degenerate bases in its recognition sequence, will fractionate DNA fragments into $4^3$ (64) or $4^4$ (256) populations respectively, based on differences in their end sequences. The cDNA is then further fractionated by digesting with other enzymes which may or may not have degenerate bases in the recognition site or the overhang region produced, if anchor primer is not used to synthesize cDNA.

(2) Ligation of the fragments to a set of adapters. The digested DNA is ligated to a series of adapters whose sequences are complementary to a subpopulation of the digested DNA pool. Since mismatches are not tolerated during ligation, it results in selective ligation of the digested DNA with perfectly matched adapter sequences.

(3) Amplification of the DNA fragments. Successfully ligated DNA fragments are amplified, for example using polymerase chain reaction (PCR), under a uniform and highly stringent PCR conditions utilizing common sequences in the adapters as primers. Below is a detailed description of various steps in the method as shown in a schematic diagram (FIG. 1).

Total RNA or poly (A)$^+$ RNA isolated from the target source is reverse transcribed to make double stranded cDNA. The primer used for the first strand cDNA synthesis is oligo (dT)$_{12-24}$, oligo (dT)$_{12-24}$V, or oligo(dT)$_{12-24}$VN with or without anchor primer at the 5'-end, wherein V is any nucleotide other than T such as A, G, or C, and N is any nucleotide A, T, G, or C. The presence of a degenerate nucleotide at the 3'-end will help to position the primer precisely at the beginning of the polyA tail. The anchor primer may incorporate sequences that may be useful later on. For example, promoter sequences for recognition by bacteriophage RNA polymerases, such as T7, T3 or SP6, may be incorporated to facilitate in vitro transcription of the inserted sequences. Second strand cDNA is synthesized by using the first strand as a template. General protocols for cDNA synthesis are, for example, described in Chapter 5 of Ausubel et al., Current Protocols in Molecular Biology, Volume 1, Greene Publishing Ass. and Wiley-Interscience, 1991. Two commonly used methods of producing cDNA from mRNA are described in Okayama and Berg, *Mol. Cell Biol.* 2: 161–170 (1982) and Gubler and Hoffman, *Gene* 25: 263–269 (1983).

In a typical procedure, total RNA or poly(A)+ RNA is converted into first strand cDNA using the enzyme reverse transcriptase. A reverse transcriptase without RNase H activity is used to eliminate degradation of the RNA template during first strand cDNA synthesis. The first strand cDNA is then used as a template to synthesize the second strand cDNA using RNaseH, *E. coli* DNA polymerase, and *E. coli* DNA ligase by Gubler-Hoffman method, thereby producing a population of ds cDNA molecules.

The double stranded DNA is digested with at least one of the special group of restriction endonucleases that produces cohesive or sticky ends and that recognizes a sequence containing degenerate bases. Depending on the genome size and the mRNA complexity, the restriction enzyme that recognizes a sequence containing 2–4 degenerate bases can be selected. Considering a normal pool of 15,000 to 20,000 mRNA species expressed in a given cell, an enzyme that has 6 base recognition site including 2–3 degenerate bases is chosen. A list of type II restriction endonucleases that recognize degenerate bases and produce cohesive or sticky ends is given in Table 1.

TABLE 1

| No. of degenerate bases | Recognition sequence | RE and isoschizomer(s) |
|---|---|---|
| 1 | GACNN_N'NNGTC | AhdI, AspEI, Eam1105I, Ec1HKI, NruGI |
| | CC'TNA_GG | AocI, AxyI, Bse21I, Bsu36I, CvnI, Eco81I |
| | GACN'N_NGTC | AspI, PflFI, PsyI, Tth111I |
| | G'GNC_C | AsuI, AspS9I, BsiZI, Cfr13I, Sau96I |
| | CC'S_GG | AsuC2I, BcnI, Cau1I, NciI |
| | G'GWC_C | AvaII, Bme18I, Eco47I, HgiEI, SinI |
| | GC'TNA_GC | BlpI, Bpu1102I, Bsp1720I, CelII |
| | CC'TNA_GC | Bpu10I |
| | CC'W_GG | BsiLI, Bst2UI, BstNI, BstOI, MvaI |
| | GAATG_CN' | BsmI |
| | ACTG_GN' | BsrI |
| | 'CCNGG_ | BssKI, ScrFI |
| | AC_N'GT | Bst4CI, TaaI, Tsp4CI |
| | C'TNA_G | BstDSI, DdeI |
| | G'GTNAC_C | BstEII, BstPI, Eco91I, Eco065I, PspEI |
| | CG'GWC_CG | CpoI, CspI, RsrII |
| | RG'GNC_CY | DraII, Eco0109I |
| | CCTNN'N_NNAGG | EcoNI, XagI |
| | GC'N_GC | Fnu4HI, Fsp4HI, ItaI |
| | G'ANT_C | HinfI |
| | 'GTNAC_ | MaeIII |
| | RG'GWC_CY | PpuMI, Psp5II, PspPPI |
| | GG'GWC_CC | SanDI |
| | A'CCWGG_T | SexAI |
| | AG'GWC_CT | Sse8647I |
| | G'AWT_C | TfiI |
| | G'CWG_C | TseI |
| | 'GTSAC_ | Tsp45I |
| 2 | GT'MK_AC | AccI, FblI |
| | G'GYRC_C | AccB7I, BanI, BshNI, Eco64I |
| | A'CRYG_T | AflIII |
| | G_WGCW'C | Alw21I, AspHI, Bbv12I, BsiHKAI |
| | C'YCGR_G | Ama87I, AvaI, BcoI, BsoBI, Eco88I |
| | G_RGCY'C | BanII, Eco24I, EcoT38I, FriOI, HgiJII |
| | C'TRYA_G | BfmI, BstSFI, SfcI, SfeI |
| | G_DGCH'C | BmyI, Bsp1286I, SduI |
| | C'CNNG_G | BsaJI, BseDI, BssECI |
| | CG_RY'CG | BsaOI, BsiEI, Bsh1285I, BstMCI, McrI |
| | GGATG_NN' | BseGI, BstF5I |
| | GCAATG_NN' | BseMI, Bse3DI, BsrDI |
| | C'CWWG_G | BssT1I, Eco130I, EcoT14I, ErhI, StyI |
| | C'CRYG_G | BstDSI, DsaI |
| | GACNN_NN'NNGTC | DrdI, DseDI |
| | C'TYRA_G | SmlI |
| 3 | CCAN_NNN'NTGG | AccB7I, PflMI, Van91I |
| | CAC_NNN'GTG | AdeI, DraIII |
| | CAG_NNN'CTG | AlwNI, CaiI |
| | GCCN_NNN'NGGC | BglI |
| | CCNN_NNN'NNGG | Bsc4I, BseLI, BsiYI, BslI |
| | GCAN_NNN'NTGC | BstAPI |
| | GCNN_NNN'NNGC | MwoI |
| 4 | GTCTCN'NNNN_ | Alw26I, BsmAI |
| | CCAN_NNNN'NTGG | BstXI |
| 5 | _NNCASTGNN' | TspRI |
| | GGCCN_NNN'NGGCC | SfiI |
| | GCAN_NNN'NTGC | BstAPI |
| 8 | CCANNNN_N'NNNTGG | XcmI |

DNA recognition sequence is shown in single stranded form from 5' to 3' orientation. Cutting of the upper strand is depicted by ' whereas cutting of the lower strand is depicted by _. Degenerate nucleotides (shown in bold face) are represented by standard convention: N=A/C/G/T; V=A/C/G; R=A/G; Y=C/T; W=A/T; S=G/C; M=A/C; K=G/T; D=A/G/T; H=A/C/T (see for details, Nomenclature Committee of the International Union of Biochemistry [1985] "Nomenclature for incompletely specified bases in nucleic acid sequences," *Eur. J Biochem.* 150: 1–5)

A subset of type II restriction endonucleases, which cut DNA several bases away from the recognition sequence, are also contemplated for use in the present invention. In case of these enzymes, the nucleotide sequence between the recognition site and cleavage site is degenerate. Following is a partial list of these enzymes:

the 4 possible nucleotides at a given position (N=4, full degeneracy), they may recognize a limited subset of nucleotides (N=2–3). For example, the recognition sequence of AflIII (5'-A'CRYG_T-3') contains 2 degenerate positions (RY) each may be occupied by one of the two purines or pyrimidines. In this case, the number of distinct DNA fragments produced will be $2^2=4$ ($N^m$, where N is 2 and m is also 2). Similarly, the number of distinct fragments produced in the case of BmyI (5'-G_DGCH'C-3') will be $3^2=9$ (N=3, m=2, D=A/G/T, H=A/C/T). In a preferred embodiment, the enzyme with a recognition sequence containing multiple degenerate bases each with full degeneracy is used in order to achieve more number of distinct fragments. For example, an enzyme recognizing a sequence with 4 fully degenerate bases (i.e. N=4 and m=4) will produce 256 distinct fragments ($N^m=4^4=256$).

TABLE 2

| Restriction enzyme | Recognition sequence | Isoschizomer(s) |
|---|---|---|
| AlwI | GGATC (4/5) | BspPI, AclWI, BinI |
| BcgI | CGANNNNNNTGC (12/10) | |
| | GCANNNNNNTCG (12/10) | |
| BciVI | GTATCC (5/6) | |
| BbsI | GAAGAC (2/6) | BpuAI, BpiI, BbvII |
| BbvI | GCAGC (8/12)* | Bst71I |
| BmrI | ACTGGG | |
| BsaI | GGTCTC (1/5) | Eco31I |
| BseRI | GAGGAG (10/8) | |
| BsgI | GTGCAG (16/14) | |
| BsmAI | GTCTC (1/5) | Alw26I |
| BsmBI | CGTCTC (1/5) | Esp3I |
| BsmF1 | GGGAC (10/14) | |
| BsmI | GAATG_C(1/−1) | BsaMI, BscCI, Mva1269I |
| BspMI | ACCTGC (4/8) | |
| BsrI | ACTG_G (1/−1) | BsrSI, BseNI, Bse1I |
| EarI | CTCTTC ((1/4) | Eam1104I, Ksp632I, Bsu6I |
| Eco57I | CTGAAG (16/14) | |
| FauI | CCCGC (4/6) | |
| FokI | GGATG (9/13) | BstF5I, BseGI |
| HgaI | GACGC (5/10) | |
| HphI | GGTGA (8/7) | AsuHPI |
| MboII | GAAGA (8/7) | |
| MmeI | TCCRAC (20/18) | |
| MnlI | CCTC (7/6) | |
| PleI | GAGTC (4/5) | SchI, PpsI |
| SapI | GCTCTTC (1/4) | |
| SfaNI | GCAT (5/9) | |
| TaqII** | GACCGA (11/9) | |
| | CACCCA (11/9) | |

*Numbers in parenthesis indicate the distance between the last (the 3'-most) nucleotide of the recognition sequence and the site of cleavage on the upper/lower strand. For example, HgaI GACGC (5/10) indicates cleavage as shown below:
5 - GACGCNNNNN↓
3'- CTGCGNNNNNNNNNN↓

Negative numbers indicate the site of cleavage upstream of the recognition sequence, and in these cases is calculated from the first (5'-most) nucleotide of the recognition sequence. **TaqII is unique as it recognizes two distinct sequences shown.

The list of enzymes shown in Tables 1 and 2 is not meant to be exhaustive. The information provided is only to illustrate the utility of some representative enzymes, and is not to be construed as limiting the scope of the instant invention. More exhaustive list of enzymes that meet the requirement of the present invention can be found in any standard reference book or in the catalogs of many commercial suppliers of the enzymes.

As it will be clear, some enzymes recognize sequences with limited degeneracy, i.e. instead of recognizing any of If the anchor primer is used for cDNA synthesis, no further digestion is necessary. If an anchor oligo(dT) primer is not used during first strand cDNA synthesis, the digested cDNA will be subjected to second enzyme with or without degeneracy in the recognition site to provide another adapter ligation and PCR priming end. The preferred enzyme(s) are chosen to produce cohesive ends upon digestion of the DNA. The number and the type of chosen enzyme is based on the pool number, desired percentage of coverage and selectivity of the PCR.

Each pool of the double digested cDNAs produced from each second enzyme digestion is further divided into $N^m$ subpools. Each individual subpool is ligated to a pair of adapters. In each pair, one adapter (ADAPTER-1) is complementary to a subset of overhangs generated by the first enzyme, while the other adapter (ADAPTER-2) is complementary to the overhang generated by the second enzyme. The number of the first adapters used for ligation will thus depend upon the distinct species of fragments generated (determined by the degeneracy of the overhang region or recognition sequence) by the digestion of cDNA with the first enzyme. For example, if the first enzyme recognizes 16 different species of sequences, because of the presence of 2 fully degenerate bases in the recognition sequence ($N^m=4^2=16$), the double digested cDNA will be further divided into 16 subpools. Each subpool will be ligated using one of the 16 different types of the first adapters, perfectly complementary to a sub-species of the cohesive ends generated by the first enzyme, and the second adapter that is perfectly complementary to the cohesive ends generated by the second enzyme. The rest of cDNA in each subpool that will not be ligated to the adapters, because of the lack of complementarity with adapters, will be eliminated in the subsequent step of PCR amplification. DNA ligases require full complementarity between the two strands in order to ligate a nick (U.S. Pat. Nos. 5,366,877 and 5,093,245). This is a critical step since the selective ligation of the digested DNA with perfectly matched adapter sequences is the basis of fractionation of DNA in the present invention.

The ligated cDNA fragments are subjected to PCR amplification using the adapter upper strands as the PCR primer. PCR amplification is restricted to <25 cycles in order to achieve the linear representation of the mRNA concentration. One of the primers is suitably labeled for detection after electrophoresis. Preferably the primer is labeled with a fluorescent dye. However, any alternative means of labeling can be employed. Besides the fragments which will be amplified and detected at the end, several kinds of fragments are also created after double digestion, but will be eliminated in PCR. These include: 1) fragments derived from the 5'-end of cDNA, which have adapters only at one end; 2) fragments derived from the 3'-end of cDNA, which have adapters only at one end; 3) enzyme II-enzyme II fragments, which although capable of being amplified, are rare; and 4) Bsa-JINN-BsaJINN fragments which are also rare.

The PCR fragments are separated, displayed, detected and analyzed. Any means of separation and display known in the art can be used including, but not limited to, electrophoretic separation and display on gel. The use of thin polyacrylamide gel, such as that used for sequencing purpose, is ideal for high resolution of DNA fragments. Any alternative means for separation and detection of DNA fragments by length, preferably with high resolution, can be used. For example, such means include, among other possible methods, column chromatography, high pressure liquid chromatography (HPLC) or physical means such as mass spectroscopy. It is also possible to use unlabeled primers in PCR combined with alternative sensitive means of detecting the separated DNA fragments. For example, silver staining of polyacrylamide gels can be used to reveal fragments (Bassam et al., *Anal. Biochem.* 196: 80–83 [1991]). Another sensitive means of detecting DNA fragments is the use of DNA intercalating dyes such as ethidium bromide, propidium iodide, acridine orange, Hoechst 33258 and Hoechst 33342. The method of detection and analysis of the pattern can be integrated and automated.

The resultant differential display can be used to identify, isolate and characterize differentially expressed genes. For example, comparison of the differential display between a normal and a diseased tissue can often yield valuable information about the genes whose activities are up-regulated or down-regulated during the course of pathogenesis. Some of the observed changes in gene expression may be causally related to the pathogenesis or may be of diagnostic value. Furthermore, it may often reveal an important physiological pathway. Genes cloned using differential display method may provide a useful target for screening therapeutic compounds or may provide a basis of a diagnostic test. Temporal changes detected using differential display might also be useful in prognosis. Differential display as outlined herein can also be used for monitoring quantitative changes in gene expression in a given cell type under different conditions. For example, change in the pattern of gene expression during various stages of growth, development or differentiation can be studied. Changes in gene expression during various phases of cell cycle in a synchronized population of cells can also be conveniently examined. A profile of gene expression in a given cell type in response to the treatment with a growth factor or cytokine can be established, and this may help elucidate mechanisms of signal transduction. Temporal changes in gene expression that accompany different stages of signal transduction can be investigated using differential display disclosed herein. Genes playing important roles in cell transformation can be isolated and characterized. Such genes may provide therapeutic targets for prevention or treatment of cancer. Furthermore, these genes may also provide diagnostic or prognostic means. The method is also applicable to the assessment of effects of drugs on gene expression wherein cells treated with or without a drug are subjected to the method described herein and comparison of the differential display of mRNA reveals the effect of drug on global gene expression.

The method disclosed herein has broad applications. The method can be used for DNA fingerprinting to detect polymorphism, i.e. determining differences in the DNA from closely related samples. It is superior to the conventional restriction length polymorphism (RFLP), which detects differences in the number and size of DNA fragments produced by digestion with a given restriction enzyme. In contrast, the method of the instant invention is more sensitive in detecting changes that are escaped in the RFLP method, since it uses more than one enzyme and higher resolution of large number of fragments on thin sequencing gel. Further, one of the uses of DNA fingerprinting is in forensic science. The method can be used for differentiating pathogenic from closely related non-pathogenic organisms. For example, *Mycobacterium tuberculosis*, a causative organism for tuberculosis in humans, is closely related to *Mycobacterium smegmatis*, which is a non-pathogenic organism and is a part of the normal microbial flora of humans. Furthermore, the method of the present invention can also be used to differentiate non-pathogenic strains of bacteria from pathogenic strains. For example, various strains of the same organism may show considerable differences in pathogenesis. Once a distinct pattern of DNA fragments (fingerprint) is established for a pathogenic organism or a pathogenic strain, it can be used for rapid diagnosis. This may be particularly useful in those instances where morphological, microbiological and biochemical criteria do not adequately and sufficiently differentiate between the organisms. By the same token, the method can also be used for molecular taxonomy i.e. molecular classification of closely related organisms such as different strains or sub-strains or isolates.

The present method is also useful, when applied to genomic DNA, in detecting chromosomal translocations, gene amplifications, loss of heterozygosity for an allele etc. This information is particularly useful in the diagnosis of various diseases with underlying changes affecting DNA such as in cancer. For example, a number of specific chromosomal translocations involving and leading to activation of cellular proto-oncogenes have been reported in cancer cells. When genomic DNA from normal and diseased (for instance, suspected of or diagnosed with cancer) state are analyzed using the disclosed method, these changes will show up as changes in the DNA profile of diseased state e.g. disappearance and appearance of certain fragments. Similarly, a number of proto-oncogenes are amplified in cancer cells. These quantitative changes will be reflected in increased intensity of certain fragments in the profile of cancer DNA as compared to normal DNA. Furthermore, the analysis carried out as per the disclosed method may also aid in the diagnosis of "loss of heterozygosity" (LOH) mutations i.e. mutation of the second (normal) allele of a tumor suppressor gene that often results in the emergence of cancer cells. The tumor suppressor genes (e.g. retinoblastoma susceptibility gene, p53, DCC, APC etc) are recessive genes, unlike proto-oncogenes which are dominant genes. Therefore, inheritance of a single mutant allele (heterozygous state) of these genes does not lead to cellular transformation. It only predisposes an individual to cancer; mutation of the second normal allele of a tumor suppressor gene in the same cell (loss of heterozygosity) leads to transformation, immortalization and finally results into tumor or cancer.

Another use of the disclosed invention concerns the construction of Expressed Sequence Tag (EST) library. A multitude of cDNA fragments generated by the method can be cloned into a suitable vector that replicates in a chosen host cells. Such transformed cells harboring all the fragments constitute an EST library, which can be screened using any of the methods available. Similarly, a library of the genomic DNA can also be prepared using the invention.

The instant invention is also applicable to plants for various agricultural uses. For example, the method can be used to examine the effect of chemical compounds on plants and agricultural related organisms, and further to establish the mode of action of such compounds. The fingerprint profiles of the cDNAs prepared from plants or fungi, treated with or without herbicide or fungicide respectively, can be compared to identify genes whose expression level is altered in response to the treatment. The temporal changes in the expression of these genes can yield valuable information regarding the mode of action of the compounds. Further optimization of the lead compounds can be performed using the established fingerprint profile.

The method can also be used for the identification of gene(s) whose expression is associated with a specific phenotype. For example, a pool of high oil and low oil corns can be profiled and compared by the invented method in order to identify the genes which may be responsible, directly or indirectly, for the observed phenotypic differences. Furthermore, the method can be used to identify compounds that can enhance or suppress a specific phenotype by following changes in the established profile in response to the treatment. For example, the rubber production of a rubber tree can be induced by the repeated cutting of the bark to collect rubber. The genes related to rubber synthesis can be identified and characterized through the comparison of differential gene expression in dormant and active rubber production trees.

Another use of the present invention in the agricultural field is the identification of genes controlling quantitative traits. Many agronomically important traits such as yield, height, stalk stability, and early vigor are quantitative traits. The method described herein can be used to study the global quantitative gene expression changes associated with those traits. The genes thus identified can then be used as markers for selection of the favored traits.

As discussed above, the present method can be used to detect polymorphism using genomic DNA or cDNA. The polymorphism information is useful for marker application. For example, in plant biology, cDNAs of different genotypes of maize can be profiled and compared to identify a marker associated with a specific trait.

The method can be used to study the isogenic lines with a deletion or change of a specific segment of chromosome, for example in maize deletion lines or maize-oat recombinant lines. Since the only change is on a specific segment of the DNA, the genomic DNA profiling can be used to identify the markers for that DNA segment. The cDNA profiling, on the other hand, will allow identification of the genes in that region, and also the functionally related genes outside of the region.

The gene(s) responsible for the mutant phenotype can be identified by comparing the gene expression profiles of mutant and wildtype plants. Similarly, the present method can be used to identify plant genes responsible for resistance to various physical, chemical or biological agents such as drought, salinity, pathogens (bacterial, viral, fungal, or insects), etc. A gene thus identified can be used as a transgene to incorporate into and modify plants that are otherwise sensitive to these agents. This is a very important application as a large amount of crops are destroyed or affected adversely, for example in yield or quality, every year as a result of these agents.

EXAMPLES

A detailed description follows to illustrate the invention as applied to mRNA profiling. However, the concept and various steps are equally applicable to and can be conveniently adapted for use in DNA profiling such as fingerprinting. In this case, the starting material is genomic DNA instead of cDNA prepared from RNA. It may be further noted that details of various steps of the disclosed invention are outlined below for illustrative purpose only. Accordingly, they are not to be interpreted to imply any limitation of the scope of the invention. Specific enzymes, reagents, experimental conditions and steps outlined below can be substituted with functional equivalents that are well known in the art. It will be clear to skilled person in the art that these equivalents are covered within the scope of the disclosed invention. Similarly, the use of commercially available reagents and kits is described only to facilitate understanding. They may be substituted by functional equivalents obtained from any alternative source or assembled in the laboratory. Various terms and general techniques described throughout the specification are in accordance with well-established convention as described, for example, in Ausubel et al., Current Protocols in Molecular Biology, Volume 1 and 2, Greene Publishing Ass. and Wiley-Interscience, New York, 1991; Sambrook et al., Molecular Cloning: A Laboratory Manual, $2^{nd}$ edition, Cold Spring Harbor Laboratory Press, Cold Spring Harbor, 1989. The method can be applied to any organism. For example, the source of cells or tissues can be a plant, a single-celled animal, a multicellular animal, a bacterium, a fungus, yeast, virus-infected cells etc. The sample can be cells grown in vitro, cells isolated from plants/animal, tissues derived from plants/animals.

Example 1

RNA Isolation

The following procedure was used for isolation of total RNA from 3 grams of tissue. However, it can be scaled up or down depending on the amount of tissue. The RNA for cDNA fingerprinting should be sufficiently pure i.e. without significant enzyme inhibitor, polysaccharide and genomic DNA contamination. Any method described in the art can be used for isolation of total RNA. One such method uses Triazol reagent described in Chomszynski et al., *Anal. Biochem.* 162: 156–159 (1987) and *Biotechniques* 15: 532–534 (1993). A protocol using RNAwiz reagent (Ambion) is described below for illustration purpose only. The RNA was dissolved in nuclease-free water or 0.1 mM EDTA. To reduce false positive results, three control samples and three treated samples were used.

A mortar and pestle were placed on dry ice and the mortar was filled with liquid nitrogen. Frozen tissue was transferred from −80° C. to dry ice or liquid nitrogen. In case of fresh tissue, it should be placed in liquid nitrogen immediately after dissection. Three grams of tissue were quickly weighed and placed immediately into the mortar that was filled with liquid nitrogen. The tissue was ground under liquid nitrogen to a fine powder, while continually adding liquid nitrogen during grinding. The powder was transferred with a small amount of liquid nitrogen to a disposable polypropylene 50 ml tube (e.g., Corning, # 430295).

After the liquid nitrogen evaporated, 30 ml of RNAwiz reagent (Ambion; 10 ml RNAwiz/per gram tissue) was immediately added to the ground tissue. The reagent and the powder were mixed thoroughly with a spatula. The tissue was not allowed to thaw until thoroughly mixed with the reagent. The sample was completely homogenized using a homogenizer (e.g., Tissue Tearor, Model 985370, 5,000–30,000 rpm, Biospec Products. Inc.), while taking care not to exceed 2 min. The sample was incubated at R.T. for 5 min. Six ml (0.2 volume of starting RNAwiz) of chloroform was added. The tube was shaken vigorously by hand for ~20 sec. and the mixture was incubated at R.T. for 10 min. The tubes were centrifuged at 4° C., 12,000×g for 15 min., and the aqueous phase (containing RNA) was carefully transferred without disturbing the semi-solid interface (containing DNA) into a new 50 ml tube. The chloroform extraction was repeated if the interface was heavy to completely remove impurities. Fifteen ml (0.5 volume of starting RNAwiz) of nuclease-free water was added, mixed well and the sample was equally divided into two 50 ml tubes. Fifteen ml (0.5 volume of starting RNAwiz) of isopropanol was added to each tube, mixed well and incubated at R.T. for 10 min. The tubes were centrifuged at 4° C., 12,000×g for 15 min. The supernatants were discarded, and the pellets were washed with ~15 ml of 70% ethanol (−20° C.) by gently vortexing. The tubes were centrifuged at 4° C., 12,000×g for 5 min. The wash was repeated once more. Ethanol was completely removed and the pellets were air dried for ~10 min. to evaporate residual ethanol. Care was taken not let the RNA dry completely, as this will make it difficult to resuspend.

The pellets from two tubes were resuspended in 0.5 ml of nuclease-free water. The tubes were centrifuged at 4° C., 12,000×g for 15 min. when the RNA solution was not clear. The supernatant was transferred to a new tube and the gelatinous pellet of polysaccharides was discarded. Contaminating genomic DNA was completely removed by performing (a) Acid-Phenol: Chloroform extraction; or (b) DNase digestion as follows:

Acid-Phenol: Chloroform Extraction

An equal volume of Acid-Phenol:Chloroform was added to RNA preparation. The tubes were shaken by hand vigorously and centrifuged at R.T., 14,000×g for 5 min. The aqueous phase was transferred to a new tube, while leaving contaminating genomic DNA in the Acid-Phenol phase. Lithium Chloride (0.5 volume of 7.5 M solution) was added to a final concentration of 2.5 M. The contents were mixed and incubated at −20° C. for 30 min. to overnight. The tubes were centrifuged at 4° C., 14,000 rpm for 20 min. The pellet was washed twice with 1 ml of 70% ethanol (−20° C.) by vortexing, centrifuged at 4° C., 14,000 rpm for 15 min, and the supernatant was removed completely. The pellet was air dried for 5–10 min. to evaporate residual ethanol, and resuspended in 0.2 ml of nuclease-free water.

DNase Digestion

The amount of RNA was estimated by measuring O.D. at 260 nm and using the following formula: RNA concentration (μg/μl)=O.D.$_{260}$×40×10$^{-3}$×dilution factor. DNase digestion was set up as below:

| | |
|---|---|
| RNA | 500 μl (assuming 500 μg) |
| RNase-free DNase 10 × buffer | 62 μl (1/10 of the final volume) |
| RNase-free DNase (1 u/μl) | 50 μl (0.1 unit/μg RNA) |
| Nuclease-free water | 8 μl |
| Final volume | 620 μl |

Reactions were incubated at 37° C. for 30 min.

An equal volume of Phenol:Chloroform:Isopropanol [25:24:1] was added. The tubes were shaken vigorously by hand and centrifuged at R.T., 14,000×g for 5 min. The aqueous phase was transferred to a new tube. Sodium Acetate (1/10 volume of 3 M solution, pH 5.5) was added, followed by the addition of 2.5 volume of absolute ethanol (−20° C.). Reactions were incubated at −20° C. overnight. Glycogen or tRNA were not added as a carrier for precipitation. The tubes were centrifuged at 4° C., 14,000 rpm for 30 min. The supernatant was removed and the pellet washed twice with 1 ml of 70% ethanol (−20° C.). The pellet was air dried for 5–10 min. to evaporate residual ethanol, and resuspended in 0.1–0.2 ml of nuclease-free water. O.D. was measured at 260, 280 and 230 nm with 100 fold dilution in 10 mM Tris-HCl (pH 7.5). The amount of RNA was calculated as described above. The purity of RNA was determined by measuring O.D.$_{260/280}$ (≧2.0 indicative of effective removal of protein) and O.D.$_{230/260}$ ratio (<0.5 indicative of effective removal of polysaccharide). A small aliquot of the total RNA (0.5–1 μg) was analyzed by formaldehyde gel electrophoresis to ensure it was not degraded.

The total RNA can further be purified to enrich Poly(A)$^+$ RNA fraction by any method described in literature e.g. Ausubel et al., Current Protocols in Molecular Biology, Volume 1 and 2, Greene Publishing Ass. and Wiley-Interscience, New York, 1991; and Sambrook et al., Molecular Cloning: A Laboratory Manual, 2$^{nd}$ edition, Cold Spring Harbor Laboratory Press, Cold Spring Harbor, 1989. Alternatively, poly(A)$^+$ RNA can also be prepared using any commercially available kit, e.g. by Oligotex mRNA Kit (Quiagen).

Example 2 cDNA Synthesis

The total RNA or poly(A)$^+$ RNA can be used for the synthesis of cDNA using any well-established method. A method of cDNA synthesis, using a commercially available kit (SuperScript Choice System from GIBCO-BRL Life Technology, Bethesda, Md.), is presented below for illustration purpose only. It will be clear to the skilled artisan that a kit from any other commercial source can be substituted for this purpose.

Two µl of oligo(dT)$_{12-18}$ primer (0.5 µg/µl) was added to 0.5–1 µg of poly (A)$^+$ RNA or 25–30 µg of total RNA, diluted as needed with diethylpyrocarbonate (DEPC)-treated water, to make a total volume of 11 µl. The mixture was heated in a 70° C. dry bath for 10 min. and quick-chilled on ice. After incubating on ice for ~5 min., the content of the tube was collected by brief centrifugation and the following reagents were added:

| | |
|---|---|
| 5 × First Strand Buffer | 4 µl |
| 0.1 M DTT | 2 µl |
| dNTP (10 mM each) | 1 µl |
| Total volume | 18 µl |

The reagents were mixed by gently tapping and collecting the contents by quick spinning. The temperature was equilibrated by placing the tube in a 37° C. or 42° C. dry bath for 2 min. Two µl of Supscript II RT (200 units/µl) was added to the tube and mixed gently by pipeting. The reaction was incubated at 37° C. for 1 hour in case of poly(A)$^+$ or 42° C. for 2 hours in case of total RNA. The content of the tube was collected by brief centrifugation. The tube was placed on ice and the following reagents were added in the order to the tube:

| | |
|---|---|
| DEPC-treated water | 91 µl |
| 5 × Second Strand Buffer | 30 µl |
| dNTP Mix (10 mM each) | 3 µl |
| E. coli DNA Ligase (10 units/µl) | 1 µl |
| E. coli DNA Polymerase (10 units/µl) | 4 µl |
| E. coli RNase H (2 units/µl) | 1 µl |
| Total volume | 150 µl |

The reaction was incubated at 16° C. for 2 hours (for poly(A)+) or 2.5 hours (for total RNA). Care was taken not let the temperature rise. The tube was placed on ice, and 10 µl of 0.5 M EDTA was added. One hundred and sixty µl of Phenol:Chloroform:Isoamyl Alcohol [25:24:1(v/v/v)] was added, and tubes were vortexed moderately until the two phases mixed. The tubes were centrifuged at R.T., 14,000×g for 5 min. and 145–150 µl of the aqueous phase was transferred to a new tube. Ammonium Acetate (75 µl of 7.5 M solution) was added, followed by the addition of 0.56 ml of absolute ethanol (−20° C.). The content was mixed and the tubes were centrifuged immediately at R.T., 14,000 rpm for 20 min. The supernatant was carefully and completely removed. The pellet was rinsed with 0.5 ml of 70% ethanol (−20° C.), and air dried for 5–10 min. in a 37° C. dry bath to evaporate residual ethanol. The amount of cDNA was estimated. Typically 0.5–1 µg or 200–250 ng of cDNA was obtained from 0.5–1 µg of poly(A)$^+$ RNA or 20–25 µg of total RNA, respectively. The pellet was dissolved in TE (1 mM Tris-Hcl [pH 7.5], 0.1 mM EDTA) at a final cDNA concentration of ~10 ng/µl.

Example 3

Restriction Enzyme Digestion

The example outlined below describes reactions that were carried out for 6 cDNA samples, three controls (C-1, C-2 and C-3) and three experimental samples (S-1, S-2 and S-3). However, the procedure can be conveniently adapted for any number of cDNA samples.

The reactions for restriction enzyme digestion for each sample were set up in 0.2 ml PCR tubes. The procedure described herein, using ApaL, BamHI, BglII, EcoRI, HindIII and NcoI enzymes, is only for illustrative purpose and is not to be construed as limiting the scope of the invention. The number of enzymes used and the types can be varied depending on the specific need. The example presented below describes total 36 reactions for three controls and three treated samples. Each reaction contained:

| | |
|---|---|
| 10 × NEBuffer$^\#$ | 3.4 µl |
| 10 × BSA (1 mg / ml) | 3.4 µl |
| Diluted 6 base-cutter enzyme (1 u / µl) | 1 µl (1 unit) |
| BsaJI (2.5 units / µl)* | 1.6 µl (4 units) |
| cDNA (~10 ng / µl) | 4 µl (~40 ng) |
| Nuclease-free water | 20.6 µl |
| Total volume | 34 µl |

$^\#$Use 10 × NEBuffer 3 (New England BioLabs) for BglII and 10 × NEBuffer 2 for all others.
*The use of restriction enzyme BsaJI is described in this example as an enzyme recognizing degenerate sequence to illustrate the procedure. It is not to be construed as limiting the scope of the disclosed invention. Any suitable restriction enzyme that recognizes degenerate bases in the recognition orcleavage sequence may be used for the purpose. A representative list of such enzymes is presented in Table 1.

The reactions were incubated at 37° C. for 1.5 hours and 60° C. for another 1.5 hours.

Example 5

Selective Ligation of Adapters

Designing Adapters

The double-stranded cDNA fragments produced by restriction digestion, as described above, were ligated with adapters. Single-stranded oligonucleotides were synthesized and annealed to form double-stranded adapters. The adapters were designed according to the following criteria: (1) The recommended length of the upper and lower strand of adapters is 18–24 and 16–18 nucleotides respectively. The upper strand of AB18-enzyme adapter is also used as the PCR 5' primer and the upper strand of CD18-BsaJ I adapter plus CNN is used as the PCR 3' primer. (2) The upper or lower strand alone and the upper strands used as PCR primers should not form stable secondary structure such as dimer or hairpin for such structures will prevent proper annealing with the complementary sequences. Similarly, the single-stranded regions (overhangs) of the adapters should not be complementary to each other in order to avoid adapter self-annealing. Additionally, both strands are used without phosphorylation in order to prevent self-ligation. (3) The adapter sequences should not contain any restriction enzyme recognition sites. (4) The adapter sequences are not significantly homologous to known gene sequences. (5) The 3'-terminal nucleotide of the upper strand should be carefully chosen so as to avoid recreating the restriction enzyme recognition site after adapter ligation. For example, T is selected as the 3'-terminal nucleotide of the upper strand of AB18-EcoRI adapter, which will ensure that the sequence generated at the junction after ligation of the adapter with EcoR I-digested fragment (TAA TTC) does not recreate the EcoRI recognition site (GAATTC).

```
    AB18-EcoR I adapter           EcoR I fragment
5' - GCTGCTAGTGTCCGATGT-------------AATTCNNNNNNNNN - 3' (SEQ ID NO: 1)

3' - GATCACAGGCTACATTAA------------GNNNNNNNNN - 5' (SEQ ID NO: 2)
```

Adapter Sequences

Following were the sequences of the adapter oligos used in the example to illustrate the strategy:

The upper strand of AB18 adapter:

5' GCTGCTAGTGTCCGATGT 3' (SEQ ID NO: 3)

The sequences of the lower strand of AB18-ApaL I, -BamH I, Bgl II, EcoRI-Hind III, and -Nco I adapters are given below. The bases in the cohesive ends generated by each enzyme are shown in bold type.

5' TGCAACATCGGACACTAG 3'(ApaL I) (SEQ ID NO: 4)
5' GATCACATCGGACACTAG 3'(BamH I) (SEQ ID NO: 5)
5' GATCACATCGGACACTAG 3'(Bgl II) (SEQ ID NO: 6)
5' AATTACATCGGACACTAG 3'(EcoR I) (SEQ ID NO: 7)
5' AGCTACATCGGACACTAG 3'(Hind III) (SEQ ID NO: 8)
5' CATGACATCGGACACTAG 3'(Nco I) (SEQ ID NO: 9)

The sequence of the upper strand of CD18 adapter:

5' GATCTCCTAGAGTCGTGA 3' (SEQ ID NO: 10)

The sequences of the lower strand of 16 kinds of CD18-BsaJ I adapters are given below. The nucleotides at degenerate positions are highlighted in bold type.

5' CTTG TCACGACTCTAG 3' (SEQ ID NO: 11)
5' CCTG TCACGACTCTAG 3' (SEQ ID NO: 12)
5' CGTG TCACGACTCTAG 3' (SEQ ID NO: 13)
5' CATG TCACGACTCTAG 3' (SEQ ID NO: 14)
5' CTCG TCACGACTCTAG 3' (SEQ ID NO: 15)
5' CCCG TCACGACTCTAG 3' (SEQ ID NO: 16)
5' CGCG TCACGACTCTAG 3' (SEQ ID NO: 17)
5' CACG TCACGACTCTAG 3' (SEQ ID NO: 18)
5' CTGG TCACGACTCTAG 3' (SEQ ID NO: 19)
5' CCGG TCACGACTCTAG 3' (SEQ ID NO: 20)
5' CGGG TCACGACTCTAG 3' (SEQ ID NO: 21)
5' CAGG TCACGACTCTAG 3' (SEQ ID NO: 22)
5' CTAG TCACGACTCTAG 3' (SEQ ID NO: 23)
5' CCAG TCACGACTCTAG 3' (SEQ ID NO: 24)
5' CGAG TCACGACTCTAG 3' (SEQ ID NO: 25)
5' CAAG TCACGACTCTAG 3' (SEQ ID NO: 26)

All oligos were cartridge or HPLC purified and were not phosphorylated to avoid adapter self ligation.

The sequences of the annealed double-stranded adapters are given below. The bases in the overhang or in the degenerate positions are shown in bold type.

```
AB18-ApaL I:    5' GCTGCTAGTGTCCGATGT 3'    (SEQ ID NO: 27)
                3' GATCACAGGCTACAACGT 5'    (SEQ ID NO: 28)

AB18-BamH II:   5' GCTGCTAGTGTCCGATGT 3'    (SEQ ID NO: 29)
                3' GATCACAGGCTACACTAG 5'    (SEQ ID NO: 30)

AB18-Bgl II:    5' GCTGCTAGTGTCCGATGT 3'    (SEQ ID NO: 31)
                3' GATCACAGGCTACACTAG 5'    (SEQ ID NO: 32)

AB18-EcoRI:     5' GCTGCTAGTGTCCGATGT 3'    (SEQ ID NO: 33)
                3' GATCACAGGCTACATTAA 5'    (SEQ ID NO: 34)

AB-18-Hind III: 5' GCTGCTAGTGTCCGATGT 3'    (SEQ ID NO: 35)
                3' GATCACAGGCTACATCGA 5'    (SEQ ID NO: 36)

AB18-Nco I:     5' GCTGCTAGTGTCCGATGT 3'    (SEQ ID NO: 37)
                3' GATCACAGGCTACAGTAC 5'    (SEQ ID NO: 38)

CD18-BsaJ I-tt  5' GATCTCCTAGAGTCGTGA 3'    (SEQ ID NO: 39)
                3'  GATCTCAGCACTGTTC 5'    (SEQ ID NO: 40)

CD18-BsaJ I-tc  5' GATCTCCTAGAGTCGTGA 3'    (SEQ ID NO: 41)
                3'  GATCTCAGCACTGTCC 5'    (SEQ ID NO: 42)

CD18-BsaJ I-tg  5' GATCTCCTAGAGTCGTGA 3'    (SEQ ID NO: 43)
                3'  GATCTCAGCACTGTGC 5'    (SEQ ID NO: 44)

CD18-BsaJ I-ta  5' GATCTCCTAGAGTCGTGA 3'    (SEQ ID NO: 45)
                3'  GATCTCAGCACTGTAC 5'    (SEQ ID NO: 46)

CD18-RsaJ I-ct  5' GATCTCCTAGAGTCGTGA 3'    (SEQ ID NO: 47)
                3'  GATCTCAGCACTGCTC 5'    (SEQ ID NO: 48)

CD18-BsaJ I-cc  5' GATCTCCTAGAGTCGTGA 3'    (SEQ ID NO: 49)
                3'  GATCTCAGCACTGCCC 5'    (SEQ ID NO: 50)

CD18-BsaJ I-cg  5' GATCTCCTAGAGTCGTGA 3'    (SEQ ID NO: 51)
                3'  GATCTCAGCACTGCGC 5'    (SEQ ID NO: 52)
```

-continued

```
CD18-BsaJ I-ca    5' GATCTCCTAGAGTCGTGA 3'        (SEQ ID NO: 53)
                  3' GATCTCAGCACTGCAC 5'          (SEQ ID NO: 54)

CD18-BsaJ I-gt    5' GATCTCCTAGAGTCGTGA 3'        (SEQ ID NO: 55)
                  3' GATCTCAGCACTGGTC 5'          (SEQ ID NO: 56)

CD18-BsaJ I-gc    5' GATCTCCTAGAGTCGTGA 3'        (SEQ ID NO: 57)
                  3' GATCTCAGCACTGGCC 5'          (SEQ ID NO: 58)

CD18-BsaJ I-gg    5' GATCTCCTAGAGTCGTGA 3'        (SEQ ID NO: 59)
                  3' GATCTCAGCACTGGGC 5'          (SEQ ID NO: 60)

CD18-BsaJ I-ga    5' GATCTCCTAGAGTCGTGA 3'        (SEQ ID NO: 61)
                  3' GATCTCAGCACTGGAC 5'          (SEQ ID NO: 62)

CD18-BsaJ I-at    5' GATCTCCTAGAGTCGTGA 3'        (SEQ ID NO: 63)
                  3' GATCTCAGCACTGATC 5'          (SEQ ID NO: 64)

CD18-BsaJ I-ac    5' GATCTCCTAGAGTCGTGA 3'        (SEQ ID NO: 65)
                  3' GATCTCAGCACTGACC 5'          (SEQ ID NO: 66)

CD18-BsaJ I-ag    5' GATCTCCTAGAGTCGTGA 3'        (SEQ ID NO: 67)
                  3' GATCTCAGCACTGAGC 5'          (SEQ ID NO: 68)

CD18BsaJ I-aa     5' GATCTCCTAGAGTCGTGA 3'        (SEQ ID NO: 69)
                  3' GATCTCAGCACTGAAC 5'          (SEQ ID NO: 70)
```

Adapter Preparation

The oligonucleotides were dissolved in TE (1 mM Tris-Hcl [pH 7.5], 0.1 mM EDTA) to make a 100 µM solution. Annealing mix was prepared for each adapter in 0.2 ml PCR tube:

| | |
|---|---|
| Nuclease-free water | 10 µl |
| 10 × annealing buffer | 2 µl |
| 100 µM upper strand | 4 µl |
| 100 µM lower strand | 4 µl |
| Total volume | 20 µl |

Tubes were placed in a Thermal Cycler with a heated lid, incubated at 65° C. for 10 min. and were allowed to cool down slowly to room temperature within 2 hours. The concentration of adapters was 20 µM. The adapters were diluted to a final concentration of 5 µM by mixing 5 µl of 20 µM adapter solution with 15 µl of Nuclease-free water, and stored at −20° C.

Adapter Ligation

Each ligation reaction contained:

| | |
|---|---|
| Restriction enzyme-digested cDNA | 2 µl (~2.5 ng) |
| 0.05 µM 6-cutter enzyme adapter | 2 µl (0.1 pmol) |
| 0.05 µM BsaJI adapter (1 of 16 kinds)* | 2 µl (0.1 pmol) |
| Ligase and buffer mix | 2 µl (1.5 units ligase) |
| Total volume | 8 µl |

Figure 2:
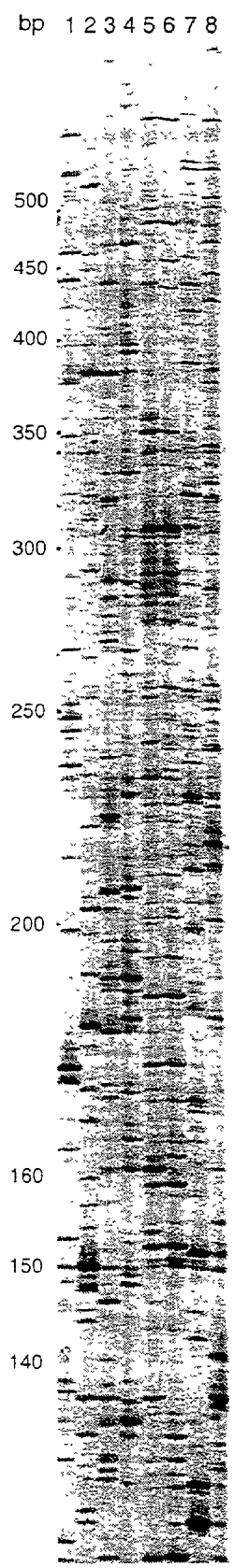
FIG. 2 is a gel image showing the specificity of adapter selective ligation. EcoRI and BsaJI double-digested mouse liver cDNA was ligated with AB18-EcoRI adapter at one end and CD18-BsaJI adapter TT, TC, TG, TA, GG, GA, AC, AG (lanes 1–8) at the other end. The ligated fragments were amplified using upper strands of AB18 and CD18 adapters as common primers.

There were 16 ligations for each digestion reaction, total 576 ligations for 36 digestion reactions. The reactions were incubated at 16° C. for 2 hours. FIG. 2 demonstrates the ligation specificity.

Example 6

Amplification of Adapter-ligated Fragments

For general description of PCR, refer to Innis et al., PCR Protocols: A Guide to Methods and Applications, Academic Press, New York, 1989; and Innis et al., PCR Strategies, Academic Press, New York, 1995.

Designing PCR Primers

Following considerations were used while designing PCR primers. The primers used for PCR (5' primer, the upper strand of AB18-enzyme adapter; 3' primer, the upper strand of CD18-BsaJ I adapter+CNN) should not be homologous to existing sequences in current nucleotide sequence database, in order to prevent multiple priming at non-specific sites during PCR. This was conveniently checked by using the candidate primer sequences to query DNA databases for finding out fortuitous complementary regions. The melting temperature ($T_m$) of the two PCR primers should be fairly close, and should be fairly high, e.g. around 55° C. This would allow the use of relatively higher annealing temperature resulting in significant reduction of non-specific amplification. The Tm, the temperature at which 50% of nucleic acid molecules are in duplex (and 50% denatured), can be reliably calculated using the nearest neighbor method (Breslauer et al., Proc. Natl. Acad. Sci. USA 83: 3746–3750 [1986]).

Some of the general considerations for designing primers for PCR are applicable here as well. For example, it is important that the primers used be highly specific for the intended target sequence and not hybridize to other sites on the template that may be partially complementary. This is particularly relevant if PCR is performed at a somewhat lower annealing temperature that would significantly allow the formation of primer-template duplexes with imperfect complementarity. The primer with a run of G/C residues at the 3'-end is likely to stably hybridize at non-target sites containing partially complementary sequences. This aspect is described by a parameter known as "internal stability" that refers to the stability of sub-sequences within an oligonucleotide, specifically to 5 base segments (pentamers) (Breslauer et al., ibid). The stability of these pentamers is described by free energy and is expressed in kcal/mol ($\Delta G$ units). An oligonucleotide with a highly stable 3'-end has a false priming tendency. A primer with low stability on its 3'-end will function well in PCR because the base pairing at and near the 3'-end with non-target sites are not sufficiently stable to initiate synthesis (false priming). Conversely, primers with stable, GC-rich, 3'-termini need not anneal with the target sequence along their entire length in order to efficiently prime, resulting often in non-specific amplification. A threshold value for ΔG can be set. For example, it is useful to set a threshold value of G at −9 kcal/mol, i.e. the ΔG of the 3'-terminal pentamer in the primer should not be less than −9 kcal/mol. Preferably, the ΔG value of the two terminal 3'-pentamers of a primer must not be less than the threshold value (Rychlik and Rhoads, *Nucleic Acids Res.* 17: 8543–8551 [1989]).

Another requirement is that the primers be free of dimers and hairpins. PCR primers should be free of significant complementarity at their 3'-termini as this promotes the formation of primer-dimer artifacts, which reduce product yield. Because of very high processivity of thermostable polymerases, very little time is required for the enzyme to recognize a 3'-terminal duplex and start polymerization. It is important to note that GC-rich regions are more stable than AT-rich regions. Furthermore, duplex stability is also governed by nearest neighbor. For example, the duplex d(AA/TT) is more stable than d(AC/GT). The stability is a function of the length, precise sequence, salt concentration, temperature etc. Primers forming hairpins or dimers function poorly in PCR. This is particularly troublesome when 3'-ends are involved in these interactions, since this can cause internal primer extension thus eliminating a given primer from the intended reaction. Thus, a primer that is complementary at its 3'-end to another primer or to itself is useless for PCR. Generally, primers with more than 3 contiguous hybridizing bases should be avoided. In general, primers forming intramolecular duplexes (e.g. hairpin) with negative ΔG should be avoided. Although, self-complementary PCR primers with hairpin stem ΔG approaching −3 kcal/mol are suitable in certain cases, a hairpin loop-forming primer is troublesome when its 3'-end is tied up, since this can cause internal primer extension, thus eliminating a given primer from the intended reaction. However, hairpins near the 5'-end do not significantly affect PCR performance. Homoologomers longer than 5 bases (AAAAAA, for example) and contiguous repetitions of two bases occurring 3 times or more (CGCGCG, for example) should be avoided in primer sequence.

A number of these parameters for determining optimal PCR conditions can be analyzed using various softwares such as OLIGO™ (National Biosciences, Inc., Plymouth, Minn.), and are integrated in some of the widely used software packages for DNA/RNA analysis available commercially.

Labeling of PCR Primer

One of the primers was labeled with fluorescent dye in order to facilitate the detection and quantitation of DNA fragments on gel. Fluorochromes that can be used for this purpose include the classic fluorochromes as well as more specialized fluorochromes. The classic fluorochromes include bimane, ethidium, europium (III) citrate, fluorescein, La Jolla blue, methylcoumarin, nitrobenzofuran, pyrenebutyrate, rhodamine, terbium chelate and tetramethylrhodamine. More specialized fluorochromes are listed in Table 3.

TABLE 3

| Fluorochrome | Supplier* | Absorption Maximum | Emission Maximum |
|---|---|---|---|
| Bodipy | Molecular Probes | 493 | 503 |
| 493/503 Cy2 | BDS | 489 | 505 |
| Bodipy FL | Molecular Probes | 508 | 516 |
| FTC | Molecular Probes | 494 | 518 |
| FluorX | BDS | 494 | 520 |
| FAM | Perkin-Elmer | 495 | 535 |
| Carboxy-rhodamine | Molecular Probes | 519 | 543 |
| EITC | Molecular Probes | 522 | 543 |
| Bodipy 530/550 | Molecular Probes | 530 | 550 |
| JOE | Perkin-Elmer | 525 | 557 |
| HEX | Perkin-Elmer | 529 | 560 |
| Bodipy 542/563 | Molecular Probes | 542 | 563 |
| Cy3 | BDS | 552 | 565 |
| TRITC | Molecular Probes | 547 | 572 |
| LRB | Molecular Probes | 556 | 576 |
| Bodipy LMR | Molecular Probes | 545 | 577 |
| Tamra | Perkin-Elmer | 552 | 580 |
| Bodipy 576/589 | Molecular Probes | 576 | 589 |
| Bodipy 581/591 | Molecular Probes | 581 | 591 |
| Cy3.5 | BDS | 581 | 596 |
| XRITC | Molecular Probes | 70 | 596 |
| ROX | Perkin-Elmer | 550 | 610 |
| Texas Red | Molecular Probes | 589 | 615 |
| Bodipy TR | Molecular Probes | 596 | 625 |
| Cy5 | BDS | 650 | 667 |
| Cy5.5 | BDS | 678 | 703 |
| DdCy5 | Beckman | 680 | 710 |
| Cy7 | BDS | 443 | 767 |
| DbCy7 | Beckman | 790 | 820 |

*The suppliers listed are Molecular Probes (Eugene, OR), Biological Detection Systems ("BDS") (Pittsburgh, PA) and Perkin-Elmer (Norwalk, CT).

Preferred method of utilizing these fluorochromes is by attaching them to particular nucleotide groups (described in Kricka et al., 1995, Molecular Probing, Blotting, and Sequencing, chap. 1, Academic Press, New York) by amino linker or phosophoramidite chemistry. Preferably, the fluorochrome labels are attached at the 5'-end of the primer, and each primer contains only one fluorochrome label to achieve easy quantitation of the labeled DNA fragments.

PCR Primer Sequences

As described above, one of the PCR primers is labeled with a suitable label for the detection of PCR amplified fragments. The present example is illustrated with the use of NED, a fluorescent label suitable for the purpose and commercially available from Perkin-Elmer (described in a User's Bulletin, June, 1997). The labeled primer for PCR (NED-upper strand of AB 18-enzyme adapter):

5' NED-GCTGCTAGTGTCCGATGT 3' (SEQ ID NO: 71)

Following is a list of 16 kinds of CD18-BsaJ I-NN (N=degenerate base) primers used for PCR (upper strand of CD18-BsaJ I adapter+CNN). The bases at degenerate positions are identified by bold type.

5' GATCTCCTAGAGTCGTGACAA 3' (SEQ ID NO: 72)
5' GATCTCCTAGAGTCGTGACAG 3' (SEQ ID NO: 73)
5' GATCTCCTAGAGTCGTGACAC 3' (SEQ ID NO: 74)
5' GATCTCCTAGAGTCGTGACAT 3' (SEQ ID NO: 75)
5' GATCTCCTAGAGTCGTGACGA 3' (SEQ ID NO: 76)
5' GATCTCCTAGAGTCGTGACGG 3' (SEQ ID NO: 77)
5' GATCTCCTAGAGTCGTGACGC 3' (SEQ ID NO: 78)
5' GATCTCCTAGAGTCGTGACGT 3' (SEQ ID NO: 79)
5' GATCTCCTAGAGTCGTGACCA 3' (SEQ ID NO: 80)
5' GATCTCCTAGAGTCGTGACCG 3' (SEQ ID NO: 81)

5' GATCTCCTAGAGTCGTGACCC 3' (SEQ ID NO: 82)
5' GATCTCCTAGAGTCGTGACCT 3' (SEQ ID NO: 83)
5' GATCTCCTAGAGTCGTGACTA 3' (SEQ ID NO: 84)
5' GATCTCCTAGAGTCGTGACTG 3' (SEQ ID NO: 85)
5' GATCTCCTAGAGTCGTGACTC 3' (SEQ ID NO: 86)
5' GATCTCCTAGAGTCGTGACTT 3' (SEQ ID NO: 87)

PCR Primers for TOPO-TA Cloning and cDNA Microarray
  5' primer: the upper strand of AB18-enzyme adapter
  3' primer: the upper strand of CD18-BsaJ I adapter PCR Primers for Direct Sequencing of PCR Products
  M13R-upper strand of AB18-enzyme adapter
  5'    GGAAACAGCTATGACCATGGCTGCTAGT-GTCCGATGT 3' (SEQ ID NO: 88)
  M13F-upper strand of CD18-BsaJ I adapter
  5'    TGTAAAACGACGGCCAGTGATCTCCTA-GAGTCGTGA 3' (SEQ ID NO: 89)
  All oligos were cartridge or HPLC purified.

Primer Preparation

The oligonucleotides were dissolved in TE (1 µM Tris-Hcl [pH 7.5], 0.1 µM EDTA) to make a 100 µM solution, diluted to 10 µM with nuclease-free water as a working solution and stored at −20° C. A suitable amount of NED-AB18-PCR primer was diluted to 10 µM with nuclease-free water. Ten µl of each of 16 kinds of CD18-BsaJ I-NN PCR primers was diluted with 90 µl of nuclease-free water in to 16 PCR tubes and stored at −20° C. All other primers were diluted to 10 µM with 90 µl of nuclease-free water and stored at −20° C. The PCR reactions were set up, each containing:

|  |  | final |
| --- | --- | --- |
| 10 × Taq DNA polymerase buffer | 2.5 µl | (1 × buffer) |
| 50 mM MgCl$_2$ | 0.75 µl | (1.5 mM) |
| 10 mM dNTP | 0.5 µl | (200 µM) |
| DMSO | 1.5 µl | (6%) |
| 10 µM NED-AB18-PCR primer | 2 µl | (20 pmol) |
| 10 µM CD18-BsaJI-NN-PCR primer | 2 µl | (20 pmol) |
| Adapter-ligated cDNA | 8 µl | (~2.5 ng) |
| Taq DNA polymerase (5 units / µl) | 0.4 µl | (2 units) |
| Nuclease-free water | 7.35 µl |  |
| Total volume | 25 µl |  |

The PCR program was run as follows:

| 94° C. for 3 min. | 1 cycle |
| --- | --- |
| 94° C. for 30 sec. |  |
| 56° C. for 30 sec. |  |
| 72° C. for 90 sec. | 25 cycles |
| 72° C. for 10 min. | 1 cycle |

Example 7

GeneScan by ABI Prism 3700 and Data Analysis

GenScan of PCR Products by ABI Prism 3700 DNA Analyzer

Figure 3:
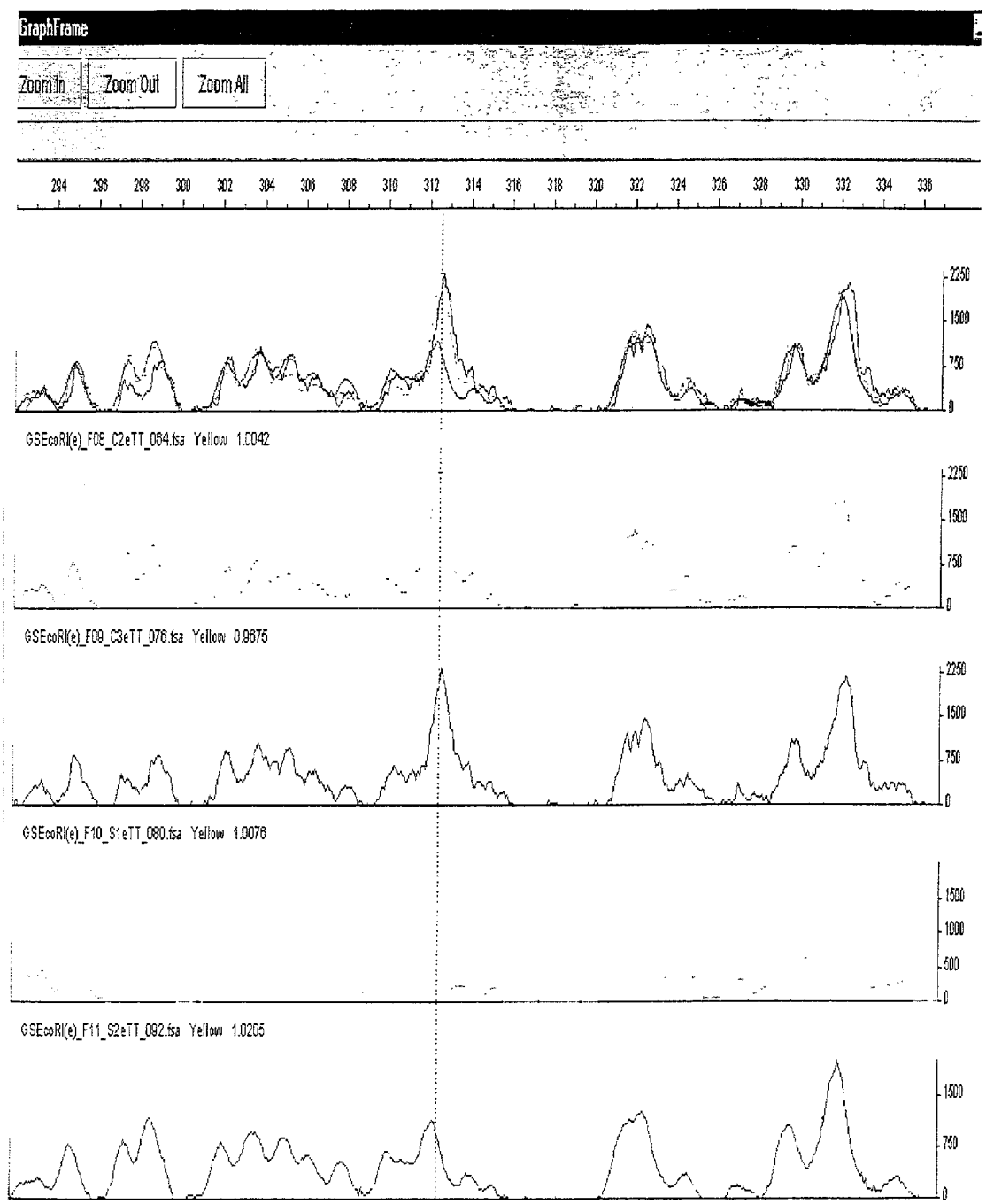
FIG. 3 is a GeneScan electropherogram from ABI Prizm 3700 showing the result of performing the method of the present invention. The starting materials is total RNA from fungi. The top panel displays the composite of the bottom four panels. The second and third panel displays the results from two individual control samples. The last two panels are the results from two independent experimental samples. Differential expression is shown as differences in peak height and area and indicated by the dotted line.
Figure 4:
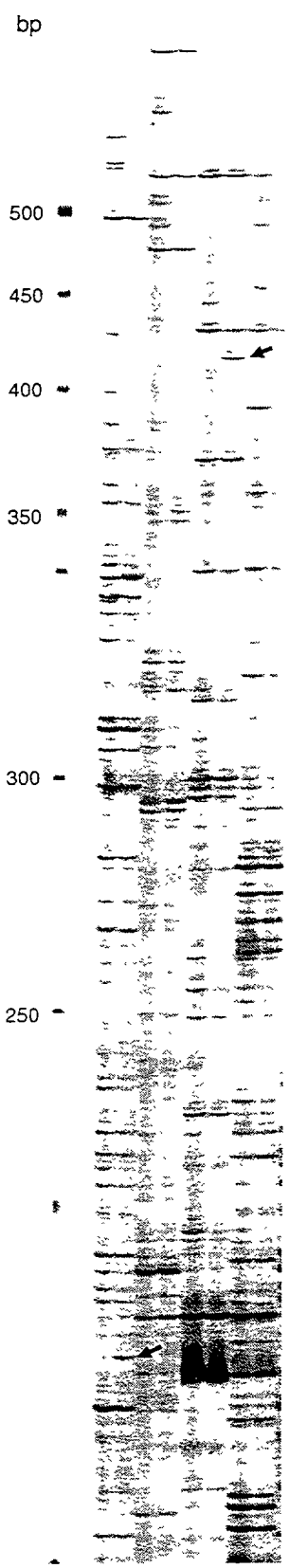
FIG. 4 is a gel image showing the result of performing the method of the present invention. The starting material is total RNA from maize leaves. The control and experimental samples are loaded pair-wise in the gel. The bands showing differential expression are indicated by the arrowheads.

Mix 3 µl of PCR products with 6 µl of deionized formamide and one µl of size standard Genescan-500 Rox. The mixtures were added in each well. The samples were denatured at 95° C. for 2 min. in a Thermal cycler with a heated lid and quick chilled on ice. The samples were run (injection time 10 sec) on ABI Prism 3700 DNA Analyzer at 35–40° C., 7500V for 4500 Sec. The data was analyzed by LEAD-Finder, an internally developed software. FIG. 3 illustrates the separation and detection of DNA fragments utilizing the present method.

Example 8

Cloning of Differentially Expressed cDNA Fragments

The selected fragments by LEAD-Finder were recovered from 5.6% denatured polyacrylamide gel as follows.

4 µl of the original PCR product was mixed with 1.5 µl of Genomyx fluoroDD Loading Dye. The samples and the size standard were denatured in a Thermal Cycler with a heated lid at 95° C. for 5 min. and quick chilling on ice. Eighty ml of HR-1000 5.6% denatured gel was mixed with 64 µl of TEMED and 640 µl of 10% Ammonium persulfate at R.T. The gel was poured and assembled quickly. Electrophoresis buffer was added (0.5×TBE in the top tank and 1×TBE in the lower tank), 4 µl of samples were loaded on the gel and electrophoresis run at 55° C., 100 W for 2 hours. The gel plate was scanned by a GenomyxSC Fluorescent Imaging Scanner. The gel image was imported in Adobe Photoshop and the bands to be recovered were marked. The gel was dried and the bands were cut using the band-marked gel image print as a reference. Each gel piece was soaked in 100 µl of TE in PCR tubes and incubated at 37° C. for 2 hours, and heated at 65° C. for 15 min. to release the DNA.

The recovered fragments were amplified by PCR (for 96 fragments). Ten µl of cDNA fragment recovered from gel were added in each well. Each PCR reaction contained:

| 10 × PCR buffer | 2 × 110 = 220.0 µl |
| --- | --- |
| 50 mM MgCl$_2$ | 0.6 × 110 = 66.0 µl |
| 10 mM dNTP | 0.4 × 110 = 44.0 µl |
| 10 µM AB18-upper strand* | 1 × 110 = 110.0 µl |
| 10 µM CD18-upper strand* | 1 × 110 = 110.0 µl |
| Taq DNA polymerase (5 units/µl) | 0.25 × 110 = 27.5 µl |
| Nuclease-free water | 4.75 × 110 = 522.5 µl |
| Total volume | 10 × 110 = 1100.0 µl |

*These primers can be substituted with M13R-AB18-upper and M13F CD18 upper PCR primers if direct sequencing of the recovered fragments is desired.

The mix (135 µl) was dispensed in 8 PCR tubes, and then 10 µl of it was dispensed to each well. The plates were placed in a Thermal Cycler with heated lid, and the PCR was programmed as follows:

| 94° C. for 3 min. | 1 cycle |
| --- | --- |
| 94° C. for 30 sec. |  |
| 56° C. for 30 sec. |  |
| 72° C. for 1.5 min. | 30 cycles |
| 72° C. for 10 min. | 1 cycle |

Five µl of 5–10 random chosen PCR products were run on 1.5% agarose gel to ensure the success of PCR. The fresh PCR products were cloned into pCR-TOPO vector (Invitrogen) under the manufacturer's instruction. Six colonies were picked from each plate (i.e., one cDNA band goes to 6 colonies) and inoculated into 150 µl of LB/Amp-8% glycerol set up in a 96 well U-bottom plate. The plates were incubated at 37° C. overnight with vigorous shaking. The cells were used to prepare PCR products for cDNA Microarray or stored at −80° C. until further use.

Example 9

Sequencing of Confirmed cDNA and GenBank Searching

Differential expression of identified genes was confirmed by cDNA Microarray, and. Once confirmed, the DNA sequence of differentially expressed cDNAs was determined and analyzed.

One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well.

What is claimed is:

1. A method for sequence-specific identification, separation, and quantitation of an amplified subset of restriction fragments in a population of restriction fragments, the method comprising:
   (a) reverse transcribing an RNA population to provide a double-stranded cDNA population;
   (b) digesting said cDNA population with one or more restriction endonucleases having a degenerate recognition or cleavage sequence, wherein said restriction endonuclease is a three- to eight-base cutter and wherein the degenerate recognition or cleavage sequence is represented by the formula $N^m$, where N is the extent of degeneracy, and m is the number of degenerate bases, and wherein for at least one of said restriction endonucleases N is 2–4 and m is 1–5, to produce restriction fragments having $N^m$ different single-stranded overhangs for each restriction endonuclease;
   (c) ligating said restriction fragments to a series of adapters lacking restriction endonuclease sites, each adapter having a sequence complementary to one of said $N^m$ different single-stranded overhangs such that restriction fragments having identical overhangs are ligated to the same adapter, wherein each ligating reaction is performed with one adapter of said series of adaptors and said one adapter can be ligated to only a subset of said $N^m$ different single-stranded overhangs on said restriction fragments;
   (d) amplifying said subset of said restriction fragments for no more than 25 cycles with a primer comprising a detectable label, wherein said primer is designed to amplify only those restriction fragments to which said one adapter of said series of adapters has been ligated, and wherein the amplifying for no more than 25 cycles produces an amplified subset of restriction fragments that are linearly representative of the RNA population; and
   (e) detecting and quantifying said amplified subset of restriction fragments.

2. The method of claim 1 wherein for at least one of said restriction endonucleases m is 2, 3, or 4.

3. The method of claim 1 wherein said restriction endonuclease comprises a four-base cutter.

4. The method of claim 1, further comprising digesting the restriction fragments obtained in (b) with one or more further restriction endonucleases to produce a plurality of restriction fragments with single-stranded overhangs on at least one end that are different from those produced in (b).

5. The method of claim 4, further comprising ligating the single-stranded overhangs produced by the digesting of claim 4 to a series of adapters, each adapter having a sequence complementary to one of said overhangs.

6. The method of claim 1 wherein said restriction fragments of (d) are amplified by the polymerase chain reaction (PCR) to produce PCR products.

7. The method of claim 6 wherein said adapters provide priming sites for said polymerase chain reaction.

8. The method of claim 6 further comprising detecting and quantifying the PCR products.

* * * * *

```
                        SEQUENCE LISTING

<160> NUMBER OF SEQ ID NOS: 89

<210> SEQ ID NO 1
<211> LENGTH: 23
<212> TYPE: DNA
<213> ORGANISM: AB18-EcoR I

<400> SEQUENCE: 1
gctgctagtg tccgatgtaa ttc                                           23

<210> SEQ ID NO 2
<211> LENGTH: 19
<212> TYPE: DNA
<213> ORGANISM: AB18-EcoR II

<400> SEQUENCE: 2
gatcacaggc tacattaag                                                19

<210> SEQ ID NO 3
<211> LENGTH: 18
<212> TYPE: DNA
<213> ORGANISM: AB18-ApaL I

<400> SEQUENCE: 3
gctgctagtg tccgatgt                                                 18

<210> SEQ ID NO 4
<211> LENGTH: 18
<212> TYPE: DNA
<213> ORGANISM: AB18-ApaL I

<400> SEQUENCE: 4
tgcaacatcg gacactag                                                 18

<210> SEQ ID NO 5
<211> LENGTH: 18
<212> TYPE: DNA
<213> ORGANISM: AB18-BamH I

<400> SEQUENCE: 5
gatcacatcg gacactag                                                 18

<210> SEQ ID NO 6
<211> LENGTH: 18
<212> TYPE: DNA
<213> ORGANISM: AB18-Bgl II

<400> SEQUENCE: 6
gatcacatcg gacactag                                                 18

<210> SEQ ID NO 7
<211> LENGTH: 18
<212> TYPE: DNA
<213> ORGANISM: Ab18-EcoR I
```

-continued

<400> SEQUENCE: 7
aattacatcg gacactag                     18

<210> SEQ ID NO 8
<211> LENGTH: 18
<212> TYPE: DNA
<213> ORGANISM: AB18-Hind III

<400> SEQUENCE: 8
agctacatcg gacactag                     18

<210> SEQ ID NO 9
<211> LENGTH: 18
<212> TYPE: DNA
<213> ORGANISM: AB18-Nco I

<400> SEQUENCE: 9
catgacatcg gacactag                     18

<210> SEQ ID NO 10
<211> LENGTH: 18
<212> TYPE: DNA
<213> ORGANISM: CD18-BsaJ

<400> SEQUENCE: 10
gatctcctag agtcgtga                     18

<210> SEQ ID NO 11
<211> LENGTH: 16
<212> TYPE: DNA
<213> ORGANISM: CD18-BsaJ I

<400> SEQUENCE: 11
cttgtcacga ctctag                       16

<210> SEQ ID NO 12
<211> LENGTH: 16
<212> TYPE: DNA
<213> ORGANISM: CD18-Bsaj

<400> SEQUENCE: 12
cctgtcacga ctctag                       16

<210> SEQ ID NO 13
<211> LENGTH: 16
<212> TYPE: DNA
<213> ORGANISM: CD18-BsaJ

<400> SEQUENCE: 13
cgtgtcacga ctctag                       16

<210> SEQ ID NO 14
<211> LENGTH: 16
<212> TYPE: DNA
<213> ORGANISM: CD18-Bsaj

<400> SEQUENCE: 14
catgtcacga ctctag                       16

<210> SEQ ID NO 15
<211> LENGTH: 16
<212> TYPE: DNA
<213> ORGANISM: CD18-Basj

-continued

```
<400> SEQUENCE: 15
ctcgtcacga ctctag                                               16

<210> SEQ ID NO 16
<211> LENGTH: 16
<212> TYPE: DNA
<213> ORGANISM: CD18-Basj

<400> SEQUENCE: 16
cccgtcacga ctctag                                               16

<210> SEQ ID NO 17
<211> LENGTH: 16
<212> TYPE: DNA
<213> ORGANISM: CD18-Bsaj

<400> SEQUENCE: 17
cgcgtcacga ctctag                                               16

<210> SEQ ID NO 18
<211> LENGTH: 16
<212> TYPE: DNA
<213> ORGANISM: CD18-BsaJ

<400> SEQUENCE: 18
cacgtcacga ctctag                                               16

<210> SEQ ID NO 19
<211> LENGTH: 16
<212> TYPE: DNA
<213> ORGANISM: CD18-BasJ

<400> SEQUENCE: 19
ctggtcacga ctctag                                               16

<210> SEQ ID NO 20
<211> LENGTH: 16
<212> TYPE: DNA
<213> ORGANISM: CD18-BasJ

<400> SEQUENCE: 20
ccggtcacga ctctag                                               16

<210> SEQ ID NO 21
<211> LENGTH: 16
<212> TYPE: DNA
<213> ORGANISM: CD18-BasJ

<400> SEQUENCE: 21
cgggtcacga ctctag                                               16

<210> SEQ ID NO 22
<211> LENGTH: 16
<212> TYPE: DNA
<213> ORGANISM: CD18-BasJ

<400> SEQUENCE: 22
caggtcacga ctctag                                               16

<210> SEQ ID NO 23
<211> LENGTH: 16
<212> TYPE: DNA
<213> ORGANISM: CD18-BsaJ
```

-continued

```
<400> SEQUENCE: 23
ctagtcacga ctctag                                                  16

<210> SEQ ID NO 24
<211> LENGTH: 16
<212> TYPE: DNA
<213> ORGANISM: CD18-BasJ

<400> SEQUENCE: 24
ccagtcacga ctctag                                                  16

<210> SEQ ID NO 25
<211> LENGTH: 16
<212> TYPE: DNA
<213> ORGANISM: CD18-BsaJ

<400> SEQUENCE: 25
cgagtcacga ctctag                                                  16

<210> SEQ ID NO 26
<211> LENGTH: 16
<212> TYPE: DNA
<213> ORGANISM: CD18-BsaJ

<400> SEQUENCE: 26
caagtcacga ctctag                                                  16

<210> SEQ ID NO 27
<211> LENGTH: 18
<212> TYPE: DNA
<213> ORGANISM: AB18-ApaL I

<400> SEQUENCE: 27
gctgctagtg tccgatgt                                                18

<210> SEQ ID NO 28
<211> LENGTH: 18
<212> TYPE: DNA
<213> ORGANISM: AB18-ApaL II

<400> SEQUENCE: 28
gatcacaggc tacaacgt                                                18

<210> SEQ ID NO 29
<211> LENGTH: 18
<212> TYPE: DNA
<213> ORGANISM: AB18-BamH I

<400> SEQUENCE: 29
gctgctagtg tccgatgt                                                18

<210> SEQ ID NO 30
<211> LENGTH: 18
<212> TYPE: DNA
<213> ORGANISM: AB18-BamH I

<400> SEQUENCE: 30
gatcacaggc tacactag                                                18

<210> SEQ ID NO 31
<211> LENGTH: 18
<212> TYPE: DNA
<213> ORGANISM: AB18-Bgl II
```

-continued

```
<400> SEQUENCE: 31
gctgctagtg tccgatgt                                              18

<210> SEQ ID NO 32
<211> LENGTH: 18
<212> TYPE: DNA
<213> ORGANISM: AB18-Bgl II

<400> SEQUENCE: 32
gatcacaggc tacactag                                              18

<210> SEQ ID NO 33
<211> LENGTH: 18
<212> TYPE: DNA
<213> ORGANISM: AB18EcoR I

<400> SEQUENCE: 33
gctgctagtg tccgatgt                                              18

<210> SEQ ID NO 34
<211> LENGTH: 18
<212> TYPE: DNA
<213> ORGANISM: AB18-EcoR I

<400> SEQUENCE: 34
gatcacaggc tacattaa                                              18

<210> SEQ ID NO 35
<211> LENGTH: 18
<212> TYPE: DNA
<213> ORGANISM: AB-18-Hind III

<400> SEQUENCE: 35
gctgctagtg tccgatgt                                              18

<210> SEQ ID NO 36
<211> LENGTH: 18
<212> TYPE: DNA
<213> ORGANISM: AB-18-HIND III

<400> SEQUENCE: 36
gatcacaggc tacatcga                                              18

<210> SEQ ID NO 37
<211> LENGTH: 18
<212> TYPE: DNA
<213> ORGANISM: AB18-Nco I

<400> SEQUENCE: 37
gctgctagtg tccgatgt                                              18

<210> SEQ ID NO 38
<211> LENGTH: 18
<212> TYPE: DNA
<213> ORGANISM: AB18-Nco I

<400> SEQUENCE: 38
gatcacaggc tacagtac                                              18

<210> SEQ ID NO 39
<211> LENGTH: 18
<212> TYPE: DNA
<213> ORGANISM: CD18-BsaJ I-tt
```

```
<400> SEQUENCE: 39
gatctcctag agtcgtga                                            18

<210> SEQ ID NO 40
<211> LENGTH: 16
<212> TYPE: DNA
<213> ORGANISM: CD18-BsaJ I-tt

<400> SEQUENCE: 40
gatctcagca ctgttc                                              16

<210> SEQ ID NO 41
<211> LENGTH: 18
<212> TYPE: DNA
<213> ORGANISM: CD18-BsaJ I-tc

<400> SEQUENCE: 41
gatctcctag agtcgtga                                            18

<210> SEQ ID NO 42
<211> LENGTH: 16
<212> TYPE: DNA
<213> ORGANISM: CD18-BsaJ I-tc

<400> SEQUENCE: 42
gatctcagca ctgtcc                                              16

<210> SEQ ID NO 43
<211> LENGTH: 18
<212> TYPE: DNA
<213> ORGANISM: CD18-BsaJ I-tg

<400> SEQUENCE: 43
gatctcctag agtcgtga                                            18

<210> SEQ ID NO 44
<211> LENGTH: 16
<212> TYPE: DNA
<213> ORGANISM: CD18-BsaJ I-tg

<400> SEQUENCE: 44
gatctcagca ctgtgc                                              16

<210> SEQ ID NO 45
<211> LENGTH: 18
<212> TYPE: DNA
<213> ORGANISM: CD18-BsaJ I-ta

<400> SEQUENCE: 45
gatctcctag agtcgtga                                            18

<210> SEQ ID NO 46
<211> LENGTH: 16
<212> TYPE: DNA
<213> ORGANISM: CD18-BsaJ I-ta

<400> SEQUENCE: 46
gatctcagca ctgtac                                              16

<210> SEQ ID NO 47
<211> LENGTH: 18
<212> TYPE: DNA
<213> ORGANISM: CD18-BsaJ I-ct
```

```
<400> SEQUENCE: 47
gatctcctag agtcgtga                                              18

<210> SEQ ID NO 48
<211> LENGTH: 16
<212> TYPE: DNA
<213> ORGANISM: CD18-BsaJ I-ct

<400> SEQUENCE: 48
gatctcagca ctgctc                                                16

<210> SEQ ID NO 49
<211> LENGTH: 18
<212> TYPE: DNA
<213> ORGANISM: CD18-BsaJ I-cc

<400> SEQUENCE: 49
gatctcctag agtcgtga                                              18

<210> SEQ ID NO 50
<211> LENGTH: 16
<212> TYPE: DNA
<213> ORGANISM: CD18-BsaJ I-cj

<400> SEQUENCE: 50
gatctcagca ctgccc                                                16

<210> SEQ ID NO 51
<211> LENGTH: 18
<212> TYPE: DNA
<213> ORGANISM: CD18-BsaJ I-cg

<400> SEQUENCE: 51
gatctcctag agtcgtga                                              18

<210> SEQ ID NO 52
<211> LENGTH: 16
<212> TYPE: DNA
<213> ORGANISM: CD18-BsaJ I-cg

<400> SEQUENCE: 52
gatctcagca ctgcgc                                                16

<210> SEQ ID NO 53
<211> LENGTH: 18
<212> TYPE: DNA
<213> ORGANISM: CD18-BsaJ I-ca

<400> SEQUENCE: 53
gatctcctag agtcgtga                                              18

<210> SEQ ID NO 54
<211> LENGTH: 16
<212> TYPE: DNA
<213> ORGANISM: CD18-BsaJ I-ca

<400> SEQUENCE: 54
gatctcagca ctgcac                                                16

<210> SEQ ID NO 55
<211> LENGTH: 18
<212> TYPE: DNA
<213> ORGANISM: CD18-BsaJ I-gt
```

-continued

```
<400> SEQUENCE: 55
gatctcctag agtcgtga                                          18

<210> SEQ ID NO 56
<211> LENGTH: 16
<212> TYPE: DNA
<213> ORGANISM: CD18-BsaJ I-gt

<400> SEQUENCE: 56
gatctcagca ctggtc                                            16

<210> SEQ ID NO 57
<211> LENGTH: 18
<212> TYPE: DNA
<213> ORGANISM: CD18-BsaJ I-gc

<400> SEQUENCE: 57
gatctcctag agtcgtga                                          18

<210> SEQ ID NO 58
<211> LENGTH: 16
<212> TYPE: DNA
<213> ORGANISM: CD18-BsaJ I-gc

<400> SEQUENCE: 58
gatctcagca ctggcc                                            16

<210> SEQ ID NO 59
<211> LENGTH: 18
<212> TYPE: DNA
<213> ORGANISM: CD18-BsaJ I-gg

<400> SEQUENCE: 59
gatctcctag agtcgtga                                          18

<210> SEQ ID NO 60
<211> LENGTH: 16
<212> TYPE: DNA
<213> ORGANISM: CD18-BsaJ I-gg

<400> SEQUENCE: 60
gatctcagca ctgggc                                            16

<210> SEQ ID NO 61
<211> LENGTH: 18
<212> TYPE: DNA
<213> ORGANISM: CD18-BsaJ I-ga

<400> SEQUENCE: 61
gatctcctag agtcgtga                                          18

<210> SEQ ID NO 62
<211> LENGTH: 16
<212> TYPE: DNA
<213> ORGANISM: CD18-BsaJ I-ga

<400> SEQUENCE: 62
gatctcagca ctggac                                            16

<210> SEQ ID NO 63
<211> LENGTH: 18
<212> TYPE: DNA
<213> ORGANISM: CD18-BsaJ I-at
```

```
<400> SEQUENCE: 63
gatctcctag agtcgtga                                                 18

<210> SEQ ID NO 64
<211> LENGTH: 16
<212> TYPE: DNA
<213> ORGANISM: CD18-BsaJ I-at

<400> SEQUENCE: 64
gatctcagca ctgatc                                                   16

<210> SEQ ID NO 65
<211> LENGTH: 18
<212> TYPE: DNA
<213> ORGANISM: CD18-BsaJ I-ac

<400> SEQUENCE: 65
gatctcctag agtcgtga                                                 18

<210> SEQ ID NO 66
<211> LENGTH: 16
<212> TYPE: DNA
<213> ORGANISM: CD18-BsaJ I-ac

<400> SEQUENCE: 66
gatctcagca ctgacc                                                   16

<210> SEQ ID NO 67
<211> LENGTH: 18
<212> TYPE: DNA
<213> ORGANISM: CD18-BsaJ I-ag

<400> SEQUENCE: 67
gatctcctag agtcgtga                                                 18

<210> SEQ ID NO 68
<211> LENGTH: 16
<212> TYPE: DNA
<213> ORGANISM: CD18-BsaJ I-ag

<400> SEQUENCE: 68
gatctcagca ctgagc                                                   16

<210> SEQ ID NO 69
<211> LENGTH: 18
<212> TYPE: DNA
<213> ORGANISM: CD18-BsaJ I-aa

<400> SEQUENCE: 69
gatctcctag agtcgtga                                                 18

<210> SEQ ID NO 70
<211> LENGTH: 16
<212> TYPE: DNA
<213> ORGANISM: CD18-BsaJ I-aa

<400> SEQUENCE: 70
gatctcagca ctgaac                                                   16

<210> SEQ ID NO 71
<211> LENGTH: 18
<212> TYPE: DNA
<213> ORGANISM: NED-AB18
```

```
<400> SEQUENCE: 71
gctgctagtg tccgatgt                                          18

<210> SEQ ID NO 72
<211> LENGTH: 21
<212> TYPE: DNA
<213> ORGANISM: CD18-BsaJ CAA

<400> SEQUENCE: 72
gatctcctag agtcgtgaca a                                      21

<210> SEQ ID NO 73
<211> LENGTH: 21
<212> TYPE: DNA
<213> ORGANISM: CD18-BsaJ CAG

<400> SEQUENCE: 73
gatctcctag agtcgtgaca g                                      21

<210> SEQ ID NO 74
<211> LENGTH: 21
<212> TYPE: DNA
<213> ORGANISM: CD18-BsaJ CAC

<400> SEQUENCE: 74
gatctcctag agtcgtgaca c                                      21

<210> SEQ ID NO 75
<211> LENGTH: 21
<212> TYPE: DNA
<213> ORGANISM: CD18-BsaJ CAT

<400> SEQUENCE: 75
gatctcctag agtcgtgaca t                                      21

<210> SEQ ID NO 76
<211> LENGTH: 21
<212> TYPE: DNA
<213> ORGANISM: CD18-BsaJ CGA

<400> SEQUENCE: 76
gatctcctag agtcgtgacg a                                      21

<210> SEQ ID NO 77
<211> LENGTH: 21
<212> TYPE: DNA
<213> ORGANISM: CD18-BsaJ CGG

<400> SEQUENCE: 77
gatctcctag agtcgtgacg g                                      21

<210> SEQ ID NO 78
<211> LENGTH: 21
<212> TYPE: DNA
<213> ORGANISM: CD18-BsaJ CGC

<400> SEQUENCE: 78
gatctcctag agtcgtgacg c                                      21

<210> SEQ ID NO 79
<211> LENGTH: 21
<212> TYPE: DNA
<213> ORGANISM: CD18-BsaJ CGT
```

```
<400> SEQUENCE: 79
gatctcctag agtcgtgacg t                                              21

<210> SEQ ID NO 80
<211> LENGTH: 21
<212> TYPE: DNA
<213> ORGANISM: CD18-BsaJ CCA

<400> SEQUENCE: 80
gatctcctag agtcgtgacc a                                              21

<210> SEQ ID NO 81
<211> LENGTH: 21
<212> TYPE: DNA
<213> ORGANISM: CD18-BsaJ CCG

<400> SEQUENCE: 81
gatctcctag agtcgtgacc g                                              21

<210> SEQ ID NO 82
<211> LENGTH: 21
<212> TYPE: DNA
<213> ORGANISM: CD18-BsaJ CCC

<400> SEQUENCE: 82
gatctcctag agtcgtgacc c                                              21

<210> SEQ ID NO 83
<211> LENGTH: 21
<212> TYPE: DNA
<213> ORGANISM: CD18-BsaJ CCT

<400> SEQUENCE: 83
gatctcctag agtcgtgacc t                                              21

<210> SEQ ID NO 84
<211> LENGTH: 21
<212> TYPE: DNA
<213> ORGANISM: CD18-BsaJ CTA

<400> SEQUENCE: 84
gatctcctag agtcgtgact a                                              21

<210> SEQ ID NO 85
<211> LENGTH: 21
<212> TYPE: DNA
<213> ORGANISM: CD18-BsaJ CTG

<400> SEQUENCE: 85
gatctcctag agtcgtgact g                                              21

<210> SEQ ID NO 86
<211> LENGTH: 21
<212> TYPE: DNA
<213> ORGANISM: CD18-BsaJ CTC

<400> SEQUENCE: 86
gatctcctag agtcgtgact c                                              21

<210> SEQ ID NO 87
<211> LENGTH: 21
<212> TYPE: DNA
<213> ORGANISM: CD18-BsaJ-CTT
```

```
<400> SEQUENCE: 87
gatctcctag agtcgtgact t                                              21

<210> SEQ ID NO 88
<211> LENGTH: 37
<212> TYPE: DNA
<213> ORGANISM: M13R

<400> SEQUENCE: 88
ggaaacagct atgaccatgg ctgctagtgt ccgatgt                             37

<210> SEQ ID NO 89
<211> LENGTH: 36
<212> TYPE: DNA
<213> ORGANISM: M13F

<400> SEQUENCE: 89
tgtaaaacga cggccagtga tctcctagag tcgtga                              36
```